(12) United States Patent
Matula et al.

(10) Patent No.: US 9,645,080 B2
(45) Date of Patent: May 9, 2017

(54) SYSTEMS, DEVICES, AND METHODS FOR SEPARATING, CONCENTRATING, AND/OR DIFFERENTIATING BETWEEN CELLS FROM A CELL SAMPLE

(71) Applicant: University of Washington Through Its Center for Commercialization, Seattle, WA (US)

(72) Inventors: Thomas Matula, Kirkland, WA (US); Andrew A. Brayman, Edmonds, WA (US); Oleg A. Sapozhnikov, Seattle, WA (US); Brian MacConaghy, Kent, WA (US); Jarred Egan Swalwell, Shoreline, WA (US); Camilo Perez, Seattle, WA (US)

(73) Assignee: University of Washington, Seattle, WA (US)

( * ) Notice: Subject to any disclaimer, the term of this patent is extended or adjusted under 35 U.S.C. 154(b) by 137 days.

(21) Appl. No.: 14/254,611

(22) Filed: Apr. 16, 2014

(65) Prior Publication Data

US 2015/0017678 A1    Jan. 15, 2015

Related U.S. Application Data

(60) Provisional application No. 61/812,617, filed on Apr. 16, 2013, provisional application No. 61/824,273, filed on May 16, 2013.

(51) Int. Cl.
*G01N 33/00* (2006.01)
*G01N 21/53* (2006.01)
(Continued)

(52) U.S. Cl.
CPC ........ *G01N 21/53* (2013.01); *B01L 3/502761* (2013.01); *B01L 3/502784* (2013.01);
(Continued)

(58) Field of Classification Search
None
See application file for complete search history.

(56) References Cited

U.S. PATENT DOCUMENTS

| 4,006,444 A | 2/1977 | Quate et al. |
| 4,361,400 A | 11/1982 | Gray et al. |
| (Continued) | | |

FOREIGN PATENT DOCUMENTS

WO    WO 2012135663 A2 * 10/2012    ........ B01L 3/502761

OTHER PUBLICATIONS

Non-Final Office Action for U.S. Appl. No. 14/138,616 mailed on Mar. 3, 2015, 14 pages.
(Continued)

*Primary Examiner* — Jill Warden
*Assistant Examiner* — Brittany Fisher
(74) *Attorney, Agent, or Firm* — Kilpatrick Townsend & Stockton LLP

(57) ABSTRACT

Embodiments are generally related to differentiating and/or separating portions of a sample that are of interest from the remainder of the sample. Embodiments may be directed towards separating cells of interest from a cell sample. In some embodiments, acoustic impedances of the cells of interest may be modified. For example, the acoustic properties of the cells of interest may be modified by attaching bubbles to the cells of interest. The cell sample may then be subjected to an acoustic wave. The cells of interest may be differentiated and/or separated from the remainder of the sample based on relative displacements and/or volumetric changes experienced by the cells of interest in response thereto. The cells of interest may be separated using a standing wave and sorted into separate channels of a flow
(Continued)

cell. Optionally, the cells may be interrogated by a light source and differentiated by signals generated in response thereto.

12 Claims, 10 Drawing Sheets

(51) Int. Cl.
  *G01N 21/64* (2006.01)
  *G01N 1/40* (2006.01)
  *B01L 3/00* (2006.01)
  *G01N 15/10* (2006.01)

(52) U.S. Cl.
  CPC ....... *G01N 1/4077* (2013.01); *G01N 21/6486* (2013.01); *B01L 3/502723* (2013.01); *B01L 2200/0652* (2013.01); *B01L 2200/0673* (2013.01); *B01L 2300/0816* (2013.01); *B01L 2300/0883* (2013.01); *B01L 2400/0436* (2013.01); *G01N 2001/4066* (2013.01); *G01N 2015/1081* (2013.01); *G01N 2021/6439* (2013.01)

(56) References Cited

U.S. PATENT DOCUMENTS

| | | |
|---|---|---|
| 4,981,580 A | 1/1991 | Auer |
| 5,348,002 A | 9/1994 | Caro |
| 5,483,469 A | 1/1996 | Van den Engh et al. |
| 5,641,457 A | 6/1997 | Vardanega et al. |
| 5,853,994 A * | 12/1998 | Gopinathan ......... G01N 29/032 422/20 |
| 6,423,007 B2 | 7/2002 | Lizzi et al. |
| 6,795,191 B2 | 9/2004 | Barbehenn |
| 7,374,744 B2 | 5/2008 | Schutt |
| 7,699,799 B2 | 4/2010 | Blanton |
| 7,804,595 B2 | 9/2010 | Matula et al. |
| 8,264,683 B2 | 9/2012 | Matula et al. |
| 8,441,624 B2 | 5/2013 | Matula et al. |
| 2004/0179200 A1 | 9/2004 | Yoon et al. |
| 2006/0290944 A1 | 12/2006 | Arnott et al. |
| 2007/0151905 A1* | 7/2007 | Wang ...................... C02F 1/325 210/97 |
| 2007/0197886 A1 | 8/2007 | Naganuma et al. |
| 2008/0245745 A1* | 10/2008 | Ward .................. G01N 1/4077 209/590 |
| 2008/0247264 A1* | 10/2008 | Gabl .................. B01F 11/0266 366/127 |
| 2009/0029870 A1* | 1/2009 | Ward ................. G01N 15/1404 506/9 |
| 2009/0316151 A1* | 12/2009 | Matula ............... G01N 15/1459 356/338 |
| 2010/0009333 A1* | 1/2010 | Auer ...................... C12N 13/00 435/2 |
| 2011/0134426 A1* | 6/2011 | Kaduchak .......... G01N 15/1404 356/337 |
| 2011/0196637 A1* | 8/2011 | Sharpe ............... G01N 15/1012 702/104 |
| 2012/0160746 A1* | 6/2012 | Thorslund ......... B01L 3/502761 209/552 |
| 2012/0225475 A1* | 9/2012 | Wagner .................. G01N 15/14 435/288.7 |
| 2013/0043170 A1* | 2/2013 | Rose .................... B01D 21/283 209/659 |
| 2013/0048565 A1* | 2/2013 | Fiering ............... A61M 1/3693 210/660 |
| 2014/0347669 A1 | 11/2014 | Matula et al. |

OTHER PUBLICATIONS

Autebert et al., "*Microfluidic: An innovative tool for efficient cell sorting*", Methods 57, 2012, pp. 297-307.

Franke et al., "*Surface acoustic wave actuated cell sorting (SAWACS)*", Lab Chip, 2010, 10, This Journal is © The Royal Society of Chemistry, 2010, pp. 789-794.

Peterson et al., "*Continuous seperation of lipid particles from erythrocytes by means of laminar flow and acoustic standing wave forces*", Lab Chip, 2005, 5, 20-22, This Journal is © The Royal Society of Chemistry, 2005, 3 pages.

Allen et al., "Dynamics of Therapeutic Ultrasound Contrast Agents", Ultrasound in Med. & Biol., vol. 28, No. 6, 2002, pp. 805-816.

Barber et al., "Light Scattering Measurements of the Repetitive Supersonic Implosion of a Sonoluminescing Bubble", Physical Review Letters, vol. 69, No. 26, Dec. 28, 1992, pp. 3839-3842.

Chen et al., "The Disappearance of Ultrasound Contrast Bubbles: Observations of Bubble Dissolution and Cavitation Nucleation", Ultrasound in Med. & Biol., vol. 28, No. 6, 2002, pp. 793-803.

Church, "The effects of an elastic solid surface layer on the radial pulsations of gas bubbles", J. Acoust. Soc. Am. 97(3), Mar. 1995, pp. 1510-1521.

Dayton et al., "Optical and Acoustical Observations of the Effects of Ultrasound on Contrast Agents", IEEE Transactions on Ultrasonics, Ferroelectrics, and Frequency Control, vol. 46, No. 1, Jan. 1999, pp. 220-232.

De Jeong et al., "Higher harmonics of vibrating gas-filled microspheres. Part Two: measurements", Ultrasonics, vol. 32, No. 6, 1994, pp. 455-459.

De Jong et al., "Higher harmonics of vibrating gas-filled microspheres. Part one: simulations", Ultrasonics, vol. 32, No. 6, 1994, pp. 447-453.

De Jong et al., "Ultrasound scattering properties of Albunex microspheres", Ultrasonics vol. 31, No. 3, 1993, pp. 175-181.

Forsberg et al., "Effect of Filling Gases on the Backscatter from Contrast Microbubbles: Theory and in vivo Measurements", Ultrasound in Med. & Biol., vol. 25, No. 8, 1999, pp. 1203-1211.

Guan et al., "Using light scattering to measure the response of individual ultrasound contrast microbubbles subjected to pulsed ultrasound in vitro", J. Acoust. Soc. Am., vol. 116, No. 5, Nov. 2004, pp. 2832-2842.

Hansen, "Mie scattering as a technique for the sizing of air bubbles", Applied Optics, vol. 24, No. 19, Oct. 1, 1985, pp. 3214-3220.

Hoff et al., "Oscillations of polymeric microbubbles: Effect of the encapsulating shell", J. Acoust. Soc. Am. 107(4), Apr. 2000, pp. 2272-2280.

Holt et al., "Mie scattering used to determine spherical bubble oscillations", Applied Optics, vol. 29, No. 28, Oct. 1, 1990, pp. 4182-4191.

Khismatullin et al., "Radial oscillations of encapsulated microbubbles in viscoelastic liquids", Physics of Fluids, vol. 14, No. 10, Oct. 2002, pp. 3534-3557.

Langley et al., "Critical-angle scattering of laser light from bubbles in water: measurements, models, and application to sizing of bubbles", Applied Optics, vol. 23, No. 7, Apr. 1, 1984, pp. 1044-1054.

Marsh et al., "Broadband Measurement of the Scattering-to-Attenuation Ration for Albunex © at 37° C.", Ultrasound in Med. & Biol., vol. 25, No. 8, 1999, pp. 1321-1324.

Marston et al., "Scattering of light by a coated bubble in water near the critical and Brewster scattering angles", SPIE vol. 925, Ocean Optics IX, 1988, pp. 308-316.

Moran et al., "Quantification of Microbubble Destruction of Three Fluorocarbon-Filled Ultrasonic Contrast Agents", Ultrasound in Med. & Biol., vol. 26, No. 4, 2000, pp. 629-639.

Morgan et al., "Experimental and Theoretical Evaluation of Microbubble Behavior: Effect of Transmitted Phase and Bubble Size", IEEE Transactions on Ultrasonics, Ferroelectrics, and Frequence Control, vol. 47, No. 6, Nov. 2000, pp. 1494-1509.

Petersson et al., "Continuous separation of lipid particles from erythrocytes by means of laminar flow and acoustic standing wave forces", Lab Chip, 5, 2005, pp. 20-22.

Postema et al., "Ultrasound-Induced Encapsulated Microbubble Phenomena", Ultrasound in Med. & Biol., vol. 30, No. 6, 2004, pp. 827-840.

(56) References Cited

OTHER PUBLICATIONS

Sboros et al., "Understanding the limitations of ultrasonic backscatter measurements from microbubble populations", Physics in Medicine and Biology 47, 2002, pp. 4287-4299.
Shi et al., "Ultrasonic Characterization of the Nonlinear Properties of Contrast Microbubbles", Ultrasound in Med. & Biol., vol. 26, No. 1, 2000, pp. 93-104.
Van Der Meer et al., "Microbubble spectroscopy of ultrasound contrast agents", J. Acoust. Soc. Am. 121(1), Jan. 2007, pp. 648-656.
Wolfrum et al., "Observations of pressure-wave-excited contrast agent bubbles in the vicinity of cells", Applied Physics Letters, vol. 81, No. 26, Dec. 23, 2002, pp. 5060-5062.
Zhang et al., "The Experimental Investigation of Ultrasonic Properties for a Sonicated Contrast Agent and Its Application in Biomedicine", Ultrasound in Med. & Biol., vol. 26, No. 2, 2000, pp. 347-351.

\* cited by examiner

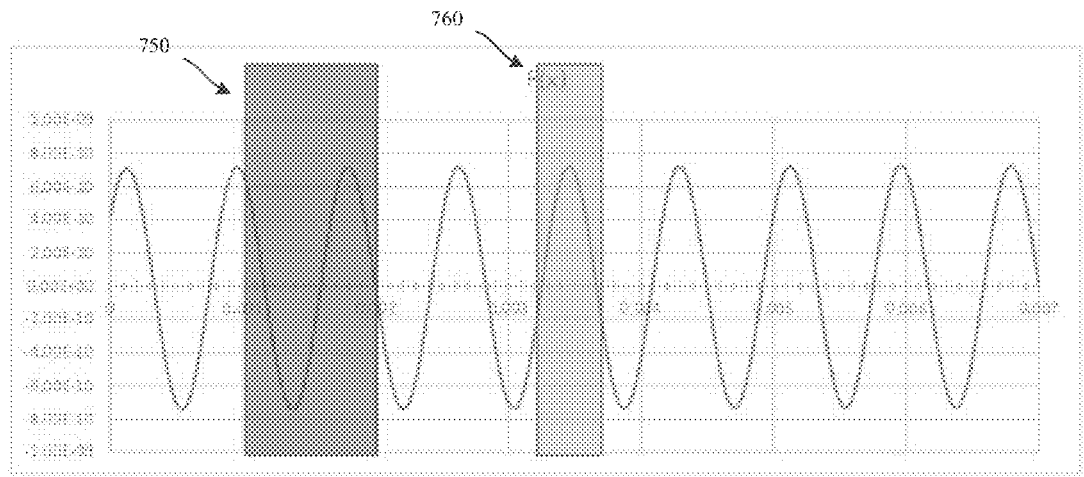
Figure 7
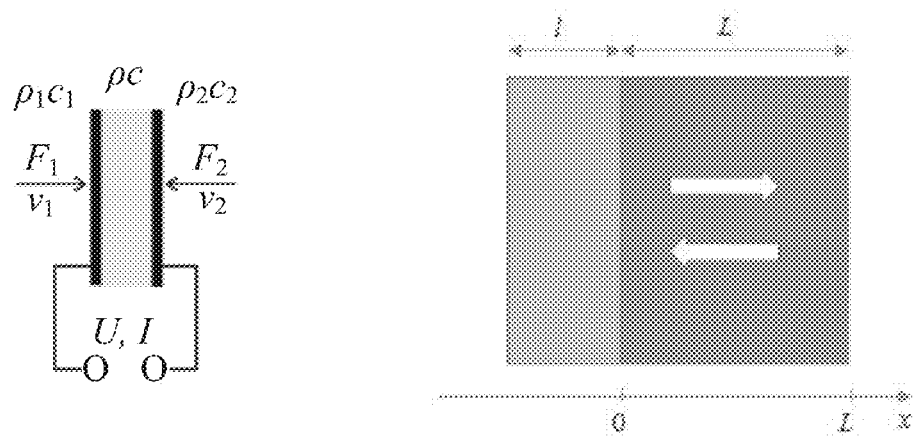
Figure 8
Figure 9

SYSTEMS, DEVICES, AND METHODS FOR SEPARATING, CONCENTRATING, AND/OR DIFFERENTIATING BETWEEN CELLS FROM A CELL SAMPLE

CROSS-REFERENCES TO RELATED APPLICATIONS

The present application claims the benefit of U.S. Provisional Patent Application No. 61/812,617 filed Apr. 16, 2013 and U.S. Provisional Patent Application No. 61/824,273 filed May 16, 2013, the disclosures of which are incorporated in their entirety herein by reference for all purposes.

BACKGROUND OF THE INVENTION

The present invention generally relates to differentiating and/or separating portions of a sample that are of interest from the remainder of the sample. For example, embodiments may be directed towards systems, devices, and methods for differentiating, separating, and/or sorting cells of interest from a cell sample.

In the development of drugs, or for the diagnosis and monitoring of disease, cells must be characterized, and often sorted for further analysis. A workhorse in this field is the flow cytometer. Measurements are performed on cells in liquid suspension, which flow one by one through a focused laser beam at rates up to several thousand cells per second. Light scattered and often the fluorescence emitted by the cells, or cell 'type'-specific fluorescent-labels attached to cells is collected, filtered, the data digitized and sent to a computer for analysis. In the research lab the technology has a number of applications. These include: cell viability assays, DNA/RNA analysis, immunophenotyping, signal transduction assays, apoptosis assays, drug resistance profiling, and protein expression analysis. Clinicians have begun to use flow cytometry for cancer and HIV diagnosis and in characterizing the likelihood of organ transplant rejection.

Flow cytometry enables three important distinctions to be made by researchers and clinicians. Flow cytometry: (1) analyzes a population of cells on a cell-by-cell basis, a critical capability for those who are looking for a relatively few very specific cells among many other cell types in a sample that will enable them to study a disease state or biological process; (2) is very rapid-routine sample analysis rates can range up to 10,000 cells per second, an incredible advance over historical methods of visually examining and counting cells; and (3) has the capacity to simultaneously measure multiple characteristics/attributes of single cells. Multi-parametric analysis allows researchers and clinicians to gather more information from a single sample faster than ever before. For example, a high-end system might have 4 lasers and be capable of processing data from as many as 18 fluorophores.

An additional feature of flow cytometers is their ability to sort cells. Cell sorting with flow cytometry is known as fluorescence activated cell sorting (FACS). In FACS, cells are funneled single-file through a narrow opening that ends in a nozzle, such that droplets of fluid emerge one at a time. Each droplet may contain one or more cells. As the droplet falls, it passes through a laser (or several lasers). If the cell is labeled with a fluorescent dye that is excited by the laser light, the fluorescence signal that it subsequently emits will be 'noted' by detectors. The scatter of the laser light, as well as the fluorescent signal(s), tells a computer to which (pre-specified) population each droplet belongs. The droplet is collected, and the computer directs the FACS instrument to send it to the appropriate location (e.g., using electric field forces). For example, it may sort droplets into categories of no cell, cell with no fluorescent signal, cell with a green fluorescent signal, cell with a red fluorescent signal, and cell with both green and red fluorescent signals.

Flow cytometers will continue to play a major role as new molecular diagnostic and monoclonal antibody tests will facilitate existing procedures and provide a basis for additional sensitive, specific and simple assays. However, presently there exist time-consuming analyses of data, including chromosomal abnormalities, DNA content, and lymphocyte subsets that reduce the effectiveness of flow cytometry. Further, the addition of capabilities adds costs, especially with new lasers and fluorescent markers. With multiple lasers and fluorophores, costs become an important consideration, as does compensation (systematic, but arbitrary reduction in signal to account for overlapping fluorescence signals), and signal/noise issues.

While advances have been made in the art of cell and/or particle sorting and filtering from a heterogeneous sample, further improvements may be desired that provide additional differentiation parameters, sorting capabilities, improve sensitivity, sort based on additional parameters based on cell type, and may do so using cost effective methods and components.

SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

A new paradigm for characterizing and/or differentiating cells, particles, and the like that improves sensitivity and sorting capabilities would have profound impact on detecting diseases and characterizing therapeutic drug outcomes. Further, systems and methods that provide for less expensive instrumentation may provide greater accessibility and lower costs per sample analysis, thereby reducing health care costs. Toward that goal, an ultrasound technology was developed to 'activate' cells passing into a region of interest in a flow cell. These activated cells may undergo volumetric changes due to the positive and negative stresses induced on the cell (showing up as a variable signal with the same rate of change as the ultrasound frequency). In some embodiments, the cells may be characterized, differentiated, and/or sorted based on the detected volumetric changes associated with the cells of interest. Further, insonated cells will also be subjected to second-order acoustic radiation forces causing displacement of the cells. In many embodiments, the cells may be characterized, differentiated, and/or sorted based on a displacement of the cells in response to the acoustic radiation forces.

In contrast to traditional systems and methods of aligning cells single-file from a heterogeneous sample of cells for processing via flow cytometry, the systems, devices, and methods of the present invention may push cells in the heterogeneous sample in a direction transverse to flow of the cells in the flow channel. Cells of interest may be displaced a distance that differentiates the cells of interest from the remainder of the cell sample. Accordingly, cells of interest may be pushed different distances and/or direction in a given time period for characterization and/or sorting. For example, in some embodiments, cells may be modified and pushed to one side of a flow channel while unmodified cells are pushed to the opposite side of the flow channel by forces generated by with an acoustic standing wave. In other embodiments, modified cells may be pushed toward the center of the flow cell while unmodified cells are pushed to the sides of the flow cell. Many alternative methods and systems are described in more detail below. In this way, differentiation, separation, filtering, and/or sorting of specific cell types (e.g., leukemia cells from a group of normal white blood cells), contaminants, particles (e.g., nanoparticles), or the like may be possible using ultrasound.

In a standing wave, bubbles go to the node or antinode depending on their size relative to the wavelength of the 'driving' acoustic wave. Specifically, the Bjerknes force (average acoustic radiation force over 1 acoustic cycle) arises from a pressure difference (gradient) across the bubble. For bubbles that are driven below their natural resonance frequency, during the negative portion of the sound field, the bubble grows. There is a pressure force on the bubble due to a slight difference in pressure exerted on either side of the bubble's surface. This force directs the bubble towards the pressure antinode. During the compressive phase of the sound field, the bubble is small, and the force is directed away from the pressure antinode. However, since the corresponding volume is smaller, this force is smaller, and hence, over an acoustic cycle the average (or Bjerknes) force directs the bubble towards the antinode. This argument on the direction of the force applies only to a bubble that is driven below its natural resonance frequency. For bubbles driven above their natural resonance frequency, a different phase response forces them away from the pressure antinode and toward a node. Since cells without attached bubbles also go to the node, in many embodiments, it may be preferable to use smaller-than-resonance bubbles so that they go to the antinode.

Advantageously, the proposed technology may primarily use ultrasound to interrogate and/or sort cells. In some embodiments, ultrasound may be used to pre-sort cells for further analysis by, for example, flow cytometry. While many embodiments may be used in conjunction with flow cytometry analysis, expensive lasers and fluorophores are not required for the sorting of cells in many embodiments. While this technology does not need to be incorporated specifically into a flow cytometer, the advantages of using the technology in addition to flow cytometers are profound. Flow cytometers are essentially multi-parametric analyzers, and thus the presently described technology adds another parameter that can be used to supplement existing analyses or create new analysis parameters based on cell type. Moreover, because flow cytometers are ubiquitous, very little further training is required in order for the ultrasound differentiation technology to help the analyst differentiate, sort, and concentrate (or enrich) cells of interest from a mixed cell sample.

Accordingly, in many embodiments, a method for differentiating cells of interest from a cell sample is provided. The method may include tagging cells of interest with bubbles by attaching bubbles to the cells of interest so as to increase the interaction between the cells of interest with an acoustic wave. After attaching the bubbles to the cells of interest, an acoustic wave may be applied to the cell sample so as to displace the cells of interest with the bubbles in the cell sample. The cells of interest with the bubbles in the cell sample may be differentiated from a remainder of the cell sample based on the displacement of the cells of interest with the bubbles in response to the applied acoustic wave.

In many embodiments, the acoustic wave may be applied to the cell sample in order to separate the cells of interest with the bubbles from the remainder of the cell sample. The method may further include delivering the cells of interest with the bubbles to a separate reservoir than a reservoir for the remainder of the cell sample in order to separately store the cells of interest. Once separated, external pressure may be applied to the cells of interest to rupture or break the attached bubbles. For example, in some embodiments, overpressure, underpressure or relatively high oscillatory pressures may be applied to the cells of interest to rupture or break the bubbles. Overpressure may be an added static pressure to force the gas out of the bubbles, effectively destroying them. Underpressure may be a partial vacuum applied to force the bubbles to grow until they grow too big and break, thereby also destroying the bubbles. Varying (dynamic, or oscillatory) pressure, not just static pressure may also be used to destroy bubbles once the cells of interest have been concentrated.

Optionally, the cells of interest with the bubbles may be differentiated in the cell sample by comparing the displacement of the cells of interest with the bubbles with the displacement of non-tagged cells in the cell sample in response to the acoustic wave—the cells with attached bubbles will experience a greater displacement in position compared to a displacement of non-tagged cells.

In some embodiments the method may include delivering the cell sample to a flow channel of a flow cell. The acoustic wave may be applied to the cell sample by an acoustic transducer acoustically coupled to the flow cell as the cell sample flows through the flow channel. In some embodiments, the acoustic wave may be a focused acoustic wave transverse to the flow channel of the flow cell. In some embodiments, a standing acoustic wave may be delivered to the cell sample in a direction transverse to the cell flow in the flow channel. The standing acoustic wave may include a pressure node and a pressure antinode. Optionally, the standing acoustic wave may be delivered so that a centerline of the flow channel is between the node and the antinode of the standing acoustic wave. The cells of interest with the bubbles may be displaced or pushed toward the antinode in response to the standing acoustic wave. In some embodiments, cells without bubble attachment in the cell sample may be displaced or pushed toward the node in response to the standing acoustic wave.

In some embodiments, the standing acoustic wave may comprise a high-order standing acoustic wave. The high-order standing acoustic wave may have a node along a centerline of the flow channel in some embodiments, and the cells of interest with the bubbles may be displaced or pushed toward sides of the flow channel in response to the high-order standing acoustic wave. Some embodiments of the method may include separating cells flowing along the sides of the flow channel from cells flowing along the centerline of the flow channel by delivering the cells to separate sub-channels or reservoirs. The cells flowing along the sides of the flow channel may comprise the cells of interest with the bubbles.

In some embodiments, the standing acoustic wave may comprise a high-order standing acoustic wave. The high-order standing acoustic wave may have an antinode along a centerline of the flow channel and the cells of interest with the bubbles may be displaced toward the centerline of the flow channel. The method may include separating cells flowing along the sides of the flow channel from cells flowing along the centerline of the flow channel into sub-channels. The cells flowing along the centerline of the flow channel may include the cells of interest with the bubbles.

In some embodiments, the cell sample may be interrogated with a light source after applying the acoustic wave to the cell sample. The method may include sorting the cells of interest into two or more subgroups based on the light source interrogation of the cells of interest. Optionally, the cells of interest may be sorted by sensing light scattered by the cells of interest with the bubbles in response to the interrogation of the cell sample with the light source. The sensed scattered light may produce a signal indicative of a vibrational effect experienced by the modified cells of interest in response to the acoustic wave. In some embodiments, the scattered light may produce a signal indicative of a type, size, thickness, or the like of a bubble attached to a cell and the cell may be sorted according to the type, size, thickness, presence, etc. of the attached bubble. Optionally, the cells of interest may be sorted by fluorescence activated cell sorting.

In some embodiments, the cells of interest may be tagged with bubbles by attaching bubbles to the cells of interest using an avidin-biotin, streptavidin-biotin or similar linkage strategy. Other systems and methods may utilize other binding strategies when there are concerns with adverse effects of these agents.

In many embodiments, a system for differentiating cells of interest from a sample is provided. The system may include an acoustic transducer and a flow cell acoustically coupled with the acoustic transducer. The flow cell may have a flow channel therethrough for conducting a sample. The acoustic transducer may be configured to deliver a standing wave transverse to the flow channel. The standing wave may have at least one node and an adjacent antinode. Further, a centerline of the flow channel may be between a node and an adjacent antinode of the standing wave.

In some embodiments, the standing wave may include only one node and the flow channel may be offset from a centerline of the flow cell. Further, in some embodiments, a downstream portion of the flow channel may split into two sub-channels or reservoirs for separating cells of interest from a remainder of the conducted sample.

A light source may be provided and configured to emit an interrogation light to the conducted sample after applying the standing wave to the conducted sample. A sensor may be included for capturing light scattered by the conducted sample in response to the interrogation light and may produce a signal indicative of a vibrational effect experienced by modified cells of the conducted sample in response to the acoustic wave. The system may also include a processor coupled to the sensor. The processor may be configured to analyze the signal to identify cells within the sample based on the vibration effect experienced by the modified cells in response to the acoustic wave.

Systems may optionally include a sensor for capturing fluorescent light emitted by cells of the conducted sample in response to the interrogation light. The sensor may produce a signal indicative of an attached fluorophore. A processor may be included that couples to the sensor. The processor may be configured to separate cells based on the detection of one or more attached fluorophores.

In some embodiments, a position sensitive detector may be included and configured to detect the translation of cells of interest in response to the standing wave. For example, photodetectors with position-sensitive signal detection can be used. Another method is to use a "knife-edge" where light passing the "knife edge" changes based on the position of the scattered particle.

In many embodiments, a system for separating cells of interest from a sample is provided. The system may include an acoustic transducer and a flow cell acoustically coupled with the acoustic transducer. The flow cell may have a flow channel therethrough for conducting a flowing sample. The acoustic transducer may be configured to deliver a standing wave transverse to the flow channel. The standing wave may have nodes and antinodes. A centerline of the flow channel may be aligned with an antinode of the standing wave.

In some embodiments, a downstream portion of the flow channel may split into three sub-channels or reservoirs for separating cells of interest from a remainder of the conducted sample. The sub-channels may include a left, a right, and a middle channel. The middle channel may be configured to receive the cells of interest.

In some systems, a light source may be configured to emit an interrogation light to the conducted sample after applying the standing wave to the conducted sample. A sensor may be provided for capturing light scattered by the conducted sample in response to the interrogation light and may thereby produce a signal indicative of a vibrational effect experienced by modified cells of the conducted sample in response to the acoustic wave. The signal may, for example, be indicative of an vibrational effect experienced by an attached bubble as bubbles exhibit oscillations in response to acoustic waves. The system may include a processor coupled to the sensor. The processor may be configured to analyze the signal to identify cells within the sample based on the vibration effect experienced by the cells in response to the acoustic wave. Optionally, the system may include a sensor for capturing fluorescing light from cells of the conducted sample in response to the interrogation light. The sensor may produce a signal indicative of an attached fluorophore. A processor may be coupled to the sensor and may be configured to separate cells based on the detection of attached fluorophores.

In many embodiments, a system for separating cells of interest from a sample is provided. The system may include an acoustic transducer and a flow cell acoustically coupled with the acoustic transducer. The flow cell may have a flow channel therethrough for receiving a sample. The acoustic transducer may be configured to deliver a standing wave transverse to the flow channel. The standing wave may have at least one node or antinode. A centerline of the flow channel may be aligned with a node of the standing wave. Further, a downstream portion of the flow channel may split into three sub-channels or reservoirs for separating cells of interest from a remainder of the conducted sample. The reservoirs may include a left, a right, and a middle channel. The left channel and the right channel may be configured to receive the cells of interest.

Optionally, embodiments of the system may include a light source configured to emit an interrogation light to the conducted sample after applying the standing wave to the conducted sample. Systems may include a sensor for capturing light scattered by the conducted sample in response to the interrogation light and may thereby produce a signal indicative of a vibrational effect experienced by cells of the conducted sample in response to the acoustic wave. Systems may include a processor coupled to the sensor—the processor may be configured to analyze the signal to identify cells within the sample based on the vibration effect experienced by the modified cells in response to the acoustic wave. Optionally, a sensor for capturing light fluorescing from cells of the conducted sample in response to the interrogation light is provided. The sensor may produce a signal indicative of an attached fluorophore. A processor may be coupled to the sensor and may be configured to separate cells based on the detection of attached fluorophores.

In some embodiments of the system, differentiation and/or separation of cells from a cell sample may be performed without a light source configured to emit an interrogation light to the conducted sample.

In many embodiments, a system for separating cells of interest from a sample is provided. The system may include an acoustic transducer and a flow cell acoustically coupled with the acoustic transducer. The flow cell may have a flow channel therethrough for receiving a sample. The acoustic transducer may be configured to deliver a focused acoustic wave transverse to the flow channel. A light source may be configured to emit an interrogation light to the conducted sample after applying the focused acoustic wave to the conducted sample. A sensor may be included for capturing light scattered by the conducted sample in response to the interrogation light and may produce a signal indicative of a vibrational effect experienced by cells of the conducted sample in response to the acoustic wave. A processor may be coupled to the sensor. The processor may be configured to analyze the signal to identify cells within the sample based on the vibration effect experienced by the cells in response to the acoustic wave.

In further embodiments, a system for separating cells of interest from a sample is provided. The system may include an acoustic transducer and a flow cell acoustically coupled with the acoustic transducer. The flow cell may have a flow channel therethrough for receiving a sample. The acoustic transducer may be configured to deliver a focused acoustic wave transverse to the flow channel. A position sensitive detector may be provided and configured to detect the positional displacement and displacement direction of cells of interest in response to the focused acoustic wave.

In further embodiments, a method for differentiating cells of interest from a cell sample is provided. The method may include modifying the cells of interest so as to increase the interaction between the cells of interest with an acoustic wave. Thereafter, the acoustic wave may be applied to the cell sample so as to displace the modified cells of interest in the cell sample. The modified cells of interest may be differentiated from a remainder of the cell sample based on the displacement of the modified cells of interest in response to the acoustic wave.

In some embodiments, the cells of interest may be modified by changing the acoustic properties of the cells of interest, for example, by loading the cells with fluorophores or other molecules. Optionally, the acoustic properties of the cells of interest may be changed by attaching bubbles to the cells of interest. In some embodiments, the cells may be immersed in a different fluid with a different viscosity.

In further embodiments, a method for differentiating cells of interest from a cell sample is provided. The method may include modifying the cells of interest so as to increase the interaction between the cells of interest with an acoustic wave. Thereafter, the acoustic wave may be applied to the cell sample. The application of the acoustic wave to the cell sample may cause the modified cells of interest to undergo volumetric changes. The cell sample may then be interrogated with a light source. The modified cells of interest may be differentiated from a remainder of the cell sample by identifying volume changes experienced by the modified cells of interest in response to the acoustic wave using the light source interrogation of the cell sample.

The invention will be better understood upon reading the following description and examining the figures which accompany it. These figures are provided by way of illustration only and are in no way limiting on the invention.

BRIEF DESCRIPTION OF THE DRAWINGS

FIG. 7 illustrates a force plot as a function of position for a system for differentiating cells;

FIG. 8 illustrates an exemplary six-pole transducer;

FIG. 9 illustrates loading of a transducer by a layer;

DETAILED DESCRIPTION

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Many embodiments of the technology relate to the use of acoustic radiation force to separate cells. Generally, cells have an intrinsic acoustic impedance very close to the fluids they are immersed in. With such a small difference, there is only a weak interaction between acoustic waves and cells. This weak interaction may make it difficult to sort cells with acoustics alone. Bubbles, on the other hand, interact very strongly with ultrasound, as their compliance and density differ by orders of magnitude from the surrounding fluid. Accordingly, in some embodiments, bubbles with specific ligands may be bound or otherwise attached to cells of interest. When the cells are exposed to acoustic fields, the bubble-cell assembly may undergo volumetric changes due to the positive and negative stresses induced on the bubble-cell assembly structure (showing up as a variable signal with the same rate of changes as the ultrasound frequency). "Bubble-cell assembly" as used herein describes one or more bubbles, reversibly or irreversibly, coupled with to a cell surface. The bubble-cell assembly may also be subjected to a second-order acoustic radiation forces causing displacement of the cells. In many embodiments, systems, methods, and devices may detect these volumetric changes and/or displacements in order to differentiate some cells from other cells in a cell sample.

Figure 1:
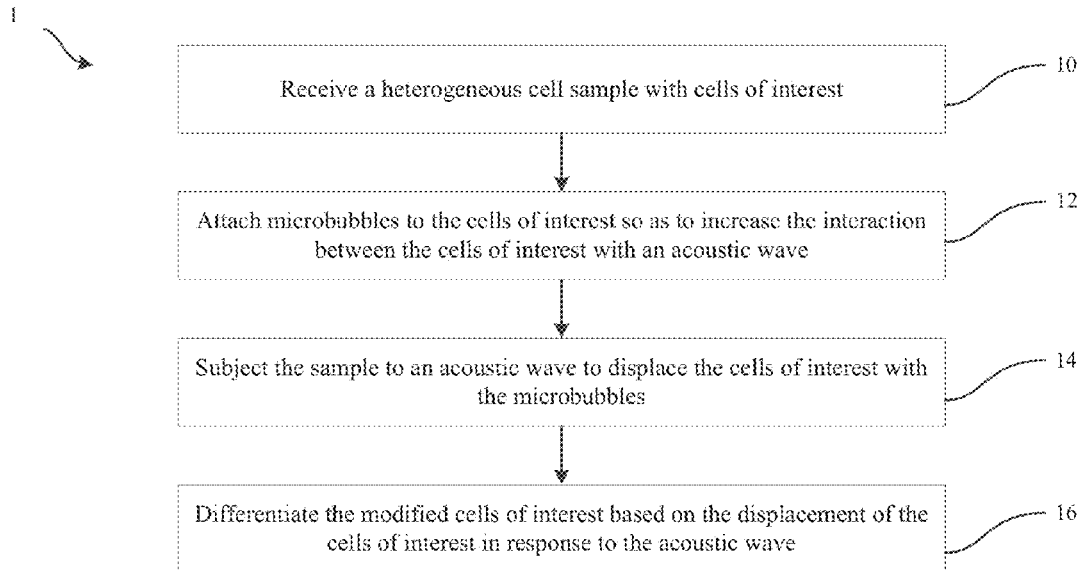
FIG. 1 illustrates a flow diagram of an exemplary method for differentiating cells of interest from a remainder of a heterogeneous cell sample according to some embodiments of the invention.

FIG. 1 illustrates a flow diagram of an exemplary method 1 for differentiating cells of interest from a remainder of a heterogeneous cell sample according to some embodiments of the invention. A heterogeneous cell sample with cells of interest may be received 10. Bubbles may be attached to the cells of interest so as to increase the interaction between the cells of interest with an acoustic wave 12. An acoustic wave may then be applied 14 to the cell sample to displace the cells of interest with the bubbles. The bubble-cell assemblies may then be differentiated from the remainder of the cell sample based at least in part on the displacement of the cells of interest in response to the acoustic wave 16. In some embodiments, a magnitude of displacement may be used to differentiate and/or cells. In some embodiments a direction of displacement may be used to differentiate and/or sort cells While discussed generally for differentiating cells from a heterogeneous cell sample, it should be understood that the above method may be used to differentiate other particles from other types of samples. For example, some methods may separate nanoparticles, contaminants, or the like from a sample using a method described above. Contaminants may be targeted using the bubbles and may thereafter be differentiated or separated from the sample using acoustic energy. Further, the method may be used to separate diseased cells from non-diseased cells, or may be used for enrichment of stem cells, or the like. The method may be used to isolate circulating tumor cells, or other types of cells that are sparse. The method may also be used to separate other particles in which bubbles can be attached to them, for example nanoparticles. In particular, a low cost and efficient system and method for isolation of diseased cells for diagnosis and isolation and enrichment of autologous stems cells for therapy may be beneficial.

Bubbles and ligands are commercially available from the field of ultrasound contrast agents. Alternatively, liposomes, or nanoparticles, or other particles that have an acoustic impedance that differs from the surrounding media may be used. Particles may be selected based in-part on their acoustic impedance properties. It may be advantageous to utilize particles with an acoustic impedance that is different from the surrounding media so that the particle will be sensitive to acoustic waves. Ultrasound contrast agent bubbles are relatively small (on the order of microns in size, e.g., 1 μm in diameter) bubbles including a shell and a core. Shells are generally implemented using lipids, polymers, and/or albumin and various other surface components, while cores are generally implemented using gases such as air, perfluoropropane (PFP), perfluorobutane (PFB), and octafluoropropane (OFP), or the like. While methods and systems are generally described as using bubbles, it should be understood that bubbles of other sizes may be used depending on the application. In some circumstances, it may be easier to tag with larger bubbles.

These bubbles may be attached to cells of interest using covalent binding strategies. There are several linkage strategies. Most common are the avidin-biotin or streptavidin-biotin ligand complexes. Antibodies attached to the ligand are specific to a cell's antigen, more specifically, to an epitope of interest. The bubble-cell assemblages are made up of a bubble with a ligand that is site specific to a target on a particular cell. Cells without the specific target (e.g., antigen) won't be bound to the bubble. The bound bubble-cell assemblage may then be "activated" using an acoustic wave.

For example, cells express different proteins (antigens) on the cell surface, and the antigens present depend on the cell type. Accordingly, cells of interest may be differentiated or distinguished from a remainder of a cell sample by identifying specific antigens which are specific to the cells of interest. Antibodies which will bind the specific cell surface antigens can be prepared, and will only interact with cells expressing that specific antigen (i.e., the cells of interest). When using a biotin-avidin or biotin-streptavidin binding strategy, the method utilizes the strong binding between the biotin protein and avidin or streptavidin. If a specific antibody is labeled with biotin, the antibody can now bind to both the cell surface antigen against which it was raised, and also to other structures which possess biotin at their surfaces. These might include biotinylated bubble shells. It is by this or similar mechanism that bubbles may be modified so that they bind to only those cells which express the antigen.

In some embodiments, the acoustic wave may be a focused acoustic wave or a standing acoustic wave generated by an acoustic transducer. In some embodiments, the sample may be placed in a flow channel of a flow cell and the acoustic wave may be delivered generally transverse to the direction of sample flow. Embodiments of systems for cell sorting are described in further detail below.

Since bubbles have very strong interactions with acoustic waves, they are easily displaced in response to the acoustic wave. Cells of interest that are attached thereto will also be displaced and will move with the attached bubble. Cells without bubbles, however, have very weak interactions with ultrasound and will move only slightly in response to the acoustic wave. Further, in some embodiments, cells with attached bubbles may be pushed in a different direction than an untagged cell. For example, when applying a standing wave to a cell sample, cells with attached bubbles an unassociated ("free") bubbles that are smaller than their resonant size are pushed toward antinodes of the standing wave, whereas cells which are not bound to bubbles are pushed toward nodes of the standing wave. Accordingly, the tagged cells may be differentiated from a remainder of the cell sample based on differences in displacement in response to the acoustic wave.

In some embodiments, portions of the cell sample may be labeled with one or more fluorophores. After activation of the bubble-cell assemblages with an acoustic wave, the cells may thereafter be further differentiated using fluorescence detection. For example, after differentiating the cells in the cell sample using the acoustic wave, the sample may be interrogated with a light source such as a laser light source. A detector may be configured to detect fluorescence from one or more fluorophore tagged cells. Accordingly, in many embodiments, cells in a cell sample may undergo a multi-parametric analysis using a combination of tagged acoustic radiation force sorting and fluorescence activated cell sorting.

In some embodiments, the applied acoustic wave may be configured to sufficiently separate the bubble-cell assemblies from the remainder of the sample. For example, in some embodiments, after the application of the acoustic wave, the bubble-tagged cells may be concentrated at particular portions of a flow channel and may subsequently flow into separate sub-channels or reservoirs from the remainder of the sample. Thus, in many embodiments, the bubble-tagged cells and the remainder of the sample may be separately stored for further analysis. In some embodiments, the bubble-tagged cells may be subjected to high oscillatory pressures, overpressure, or underpressure for the purpose of rupturing the attached bubbles.

Figure 2:
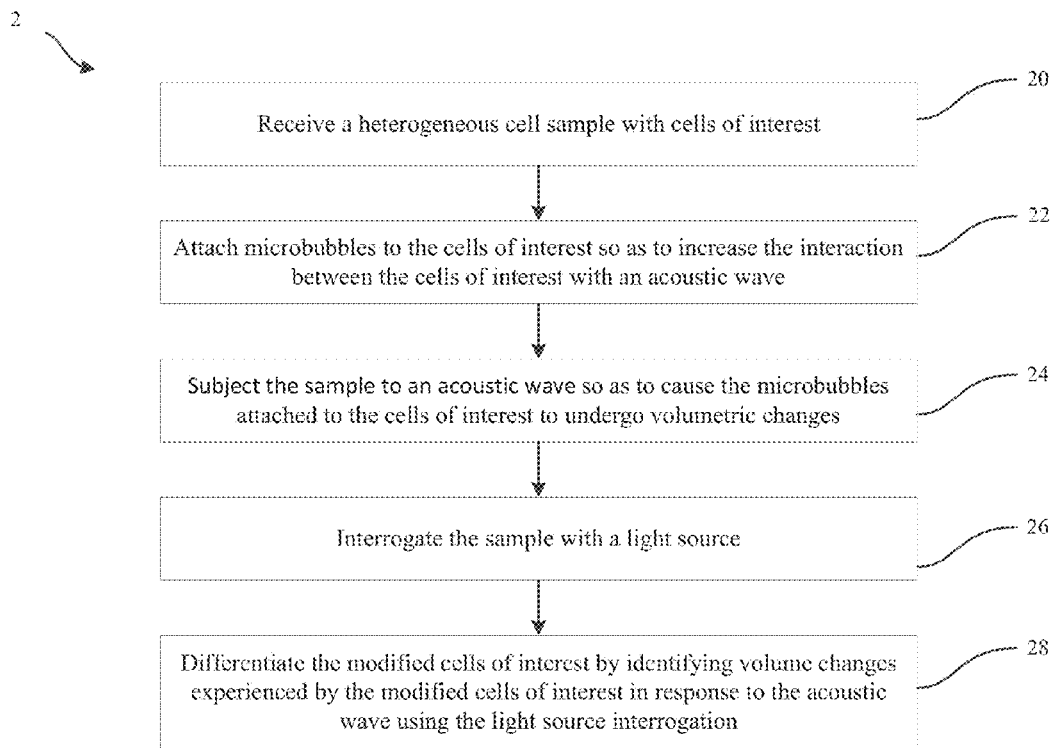
FIG. 2 illustrates a flow diagram of another exemplary method of differentiating cells of interest from a remainder of a cell sample.

FIG. 2 illustrates a flow diagram of another exemplary method 2 of differentiating cells of interest from a remainder of a cell sample. A heterogeneous cell sample with cells of interest may be received 20. Bubbles may be attached to the cells of interest so as to increase the interaction between the cells of interest with an acoustic wave 22. An acoustic wave may then be applied 24 to the cell sample to cause the bubbles attached to the cells of interest to undergo volumetric changes. The sample may be interrogated with a light source 26 and the light scattered by the cells with the attached bubbles may undergo changes due to the oscillation or vibration of the attached bubbles in response to the acoustic wave. The cells of interest with the attached bubbles may then be differentiated from the remainder of the cell sample by identifying the cells based on detected volume changes/vibrations from the modified cells of interest.

As described above, when exposed to acoustics, the bubble-cell assembly may undergo vibrations, oscillations, or volumetric changes due to the positive and negative stresses induced on the bubble-cell assembly (showing up as a variable signal with the same rate of changes as the ultrasound frequency). The scattering intensity data from the cell sample in response to the light interrogation may be used to differentiate cells with attached bubbles from cells without attached bubbles. For example, a lock-in amplifier may be used to extract the specific vibrational signal associated with the frequency that drives the bubble oscillations. This may be used to detect signals of bubbles of different sizes, or bubbles that are attached to the cells of interest, since they will have different loading. Alternatively, changes in fluorescence intensity associated with the vibration, with or without position sensitive detection can be used to differentiate the cells of interest. In a flow cell, a controller may be coupled with a sorting component to sort cells per their dynamic intensity spectrum. For example, a controller may compare the detected intensity spectrum of a cell with a database of previously determined intensity spectrums of bubble targets. Sorting components may then direct the particle to a reservoir dedicated to collecting the target particles.

If different concentrations of cells and/or bubbles are used, the acoustic wave frequency may be adjusted to maintain an acoustic standing wave in the device. In some embodiments, a phase lock loop comparator may be used to monitor and control the resonance quality so as to maintain the resonance structure.

While discussed generally for differentiating cells from a heterogeneous cell sample, it should be understood that the above method may be used to differentiate other particles from other types of samples. Further in some embodiments, fluorophores may be attached to the cells and the cells may be further analyzed by detecting emitted fluorescence from some of the cells in response to light interrogation.

Figure 3:
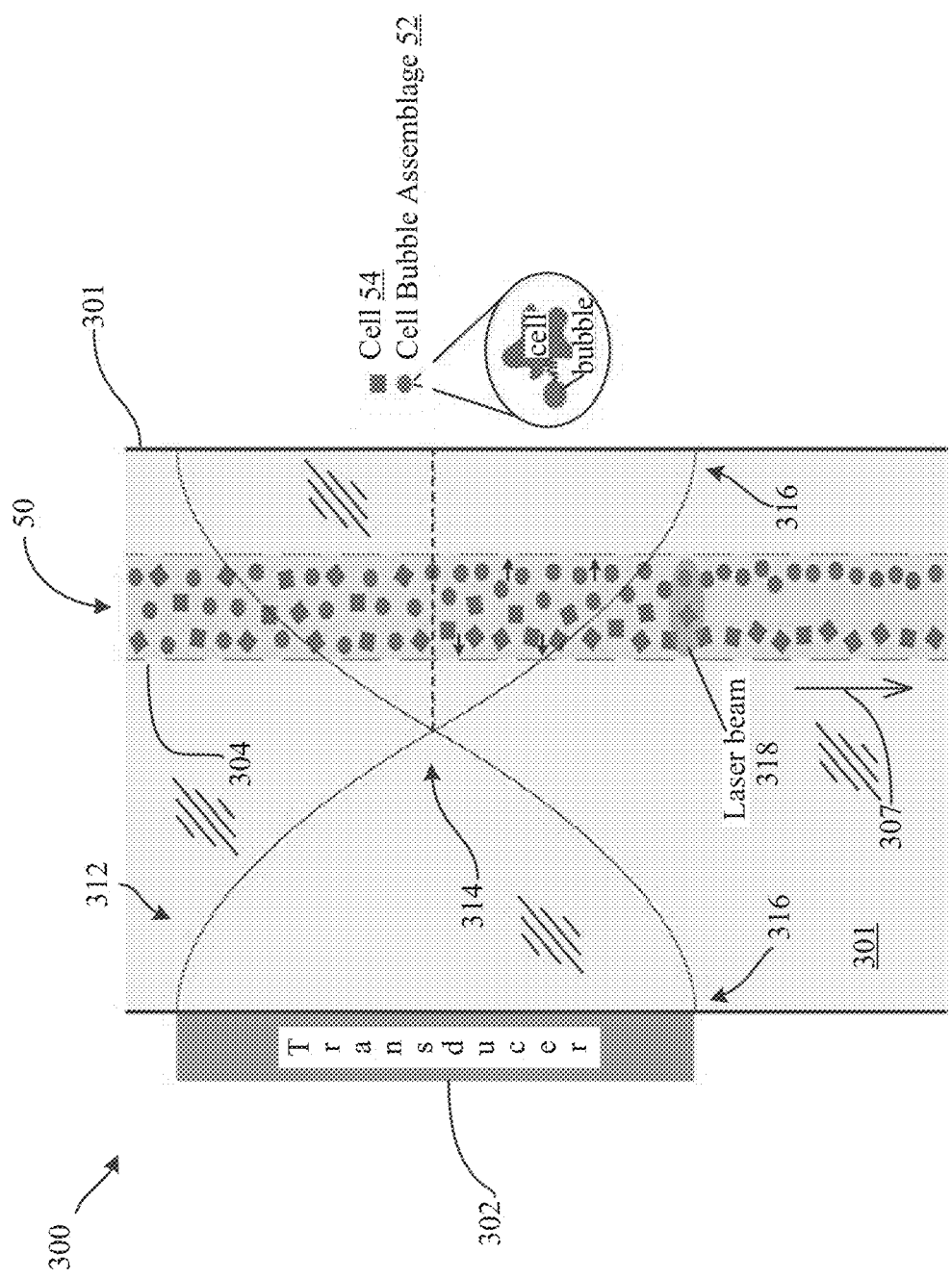
FIG. 3 illustrates an exemplary system for differentiating cells according to many embodiments of the present invention.

FIG. 3 illustrates an exemplary system 300 for differentiating cells according to methods described above. System 300 includes a flow cell 301 acoustically coupled with an acoustic source 302. The flow cell includes a flow channel 304 for receiving a sample 50. Sample 50 may be directed to flow in direction 307 and may be a heterogeneous cell sample including cells of interest 52 which are tagged with bubbles and cells which are not tagged with bubbles 54. There may also be free bubbles not attached to anything; these are not shown in the figure. The bubble-cell assemblies 52 are generally represented as circles and the untagged cells 54 are generally represented as squares.

The acoustic source may be a transducer configured to deliver a standing wave 312 to the flow cell 301. The standing wave 312 may be delivered as the sample 50 flows through the flow channel 304 and may be transverse to the flow channel 304. The standing wave 312 may have a pressure node 314 and pressure antinodes 316. The flow channel 304 may be positioned off center from the longitudinal center of the flow cell 301 such that the flow channel 304 is between the pressure node 314 and the adjacent pressure antinode 316 so that there is a pressure gradient in the flow channel 304.

As described above, cells generally have a weak interaction with acoustic waves. However, a bubble-cell assemblage 52 has a very strong interaction with sound, and may be easily pushed by sound. Further, untagged cells 54 move toward pressure nodes 314, while bubble-cell assemblages 52 will move to pressure antinodes 316, provided the bubbles are driven below their natural resonance frequency. Accordingly, by positioning the flow channel 304 between a pressure node 314 and a pressure antinode 316, un-tagged cells 54 may be separated from tagged cells 52 with a standing acoustic wave 312, because the untagged cells 54 will move (slightly) to the node, 314 while tagged cells 52 attached to bubbles will move (strongly) to pressure antinode 316. Accordingly, cells 52, 54 travel through the channel 304 mixed, but separate when in the acoustic field. Cells 54 move to the pressure node 314, while bubble-cell assemblages 52 move to the pressure antinode 316.

In many embodiments, a light source such as a laser beam 318 may be used to interrogate the sample 50 after the cells 52, 54 have been separated. The light source interrogation 318 may be part of further cell sorting by using fluorescence detection for example. In some embodiments, the light source 318 interrogation may be used to further sort the cells 52, 54 based on a difference in light scattering between bubble-cell assemblages 52 and cells 54. Further, cells of interest 52 may be further sorted based on light scattering characteristics of the attached bubbles.

In some embodiments, the acoustically tagged cell sorter may be part of a flow cytometer, especially if further analysis is needed, or as a separate sample enrichment device. In a flow cytometer setting, fluorescence detection can provide additional information as well. Further, fluorescence activated cell sorting (FACS) is generally a part of flow cytometry, so implementing tagged acoustic radiation force sorting for sorting the sub population of bound bubble-cell assemblages may be advantageous. However, the technology may be applied to many systems in which a node 314 and antinode 316 can be set up, allowing for separation of the cells 52, 54 prior to additional characterization or analyzer systems, or culturing, for example.

Figure 4:
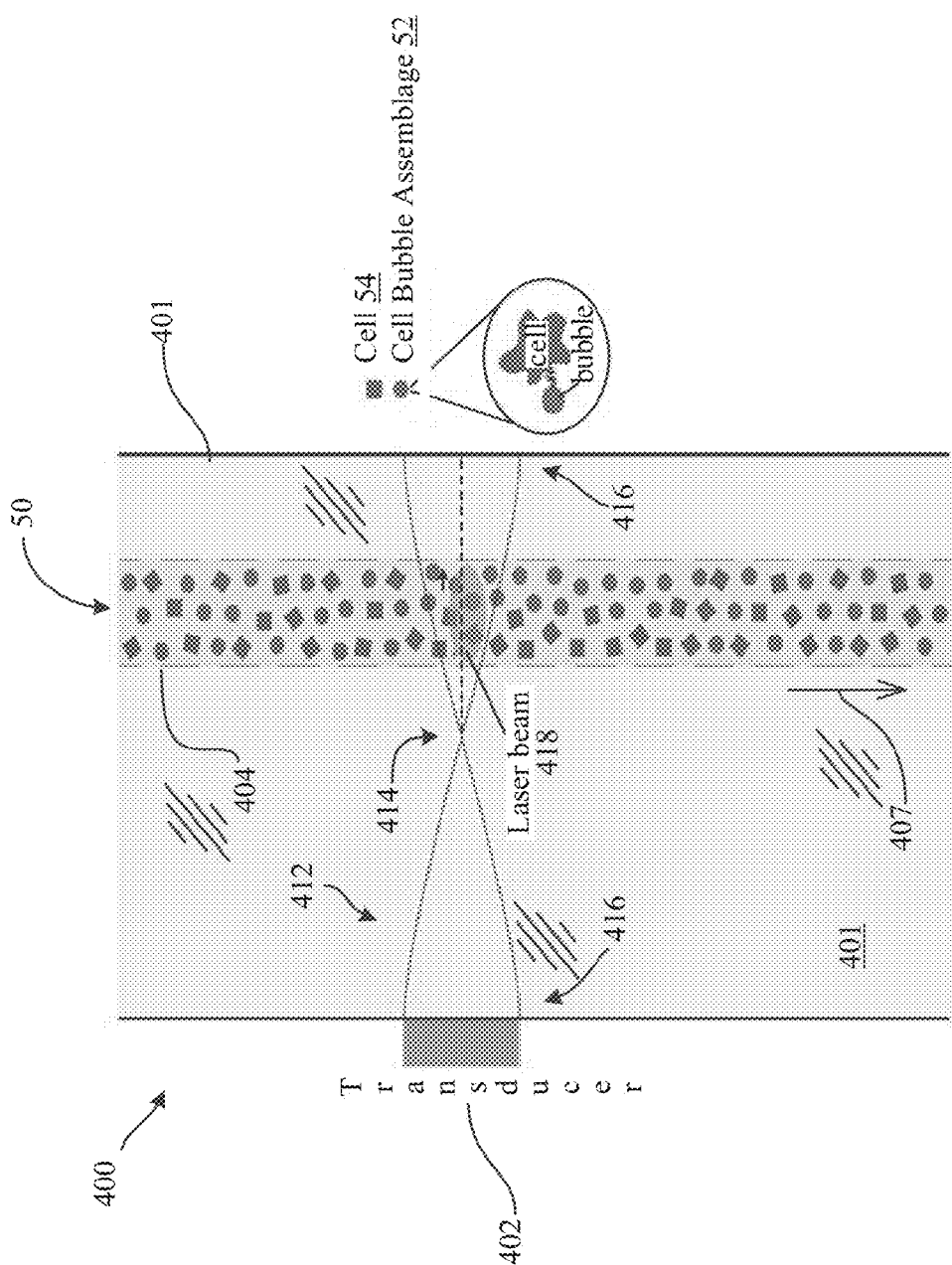
FIG. 4 illustrates another exemplary system for differentiating cells according to many embodiments of the present invention.

FIG. 4 illustrates an exemplary system 400 for differentiating cells. System 400 is similar to system 300 except system 400 may use a focused (standing or travelling) acoustic transducer 402. The acoustic transducer 402 is acoustically coupled with flow cell 401. The flow cell 401 includes a flow channel 404 for receiving a sample 50 and directing the sample in direction 407. Transducer 402 may be configured to deliver a weaker standing acoustic wave 412 transverse to the flow channel 404 with node 414 and antinodes 416. When a weaker acoustic field 412 is used, the cells 52 and the cells 54 may not completely separate in response to exposure to the standing wave 412. However, the bubble-cell assemblages 52 and the cells 54 may still be differentiated by interrogating the cells 52, 54 with a light source 418 (e.g., laser beam) while the cells 52, 54 are in the acoustic field and using position sensitive detectors to detect and compare the displacement of the cells 52 to the cells 54. Similar to the flow cell 301, the flow channel 404 may be offset from the centerline of flow cell 401 so that the cells and bubble-cell assemblages are in a pressure gradient. In some embodiments, the light source 418 interrogation may be used to further sort the cells 52, 54, not only by detecting a displacement or a direction of displacement, but also based on a difference in light scattering between bubble-cell assemblages 52 and cells 54. Further, cells 52 may be further sorted based on light scattering characteristics of the attached bubbles.

Figure 5:
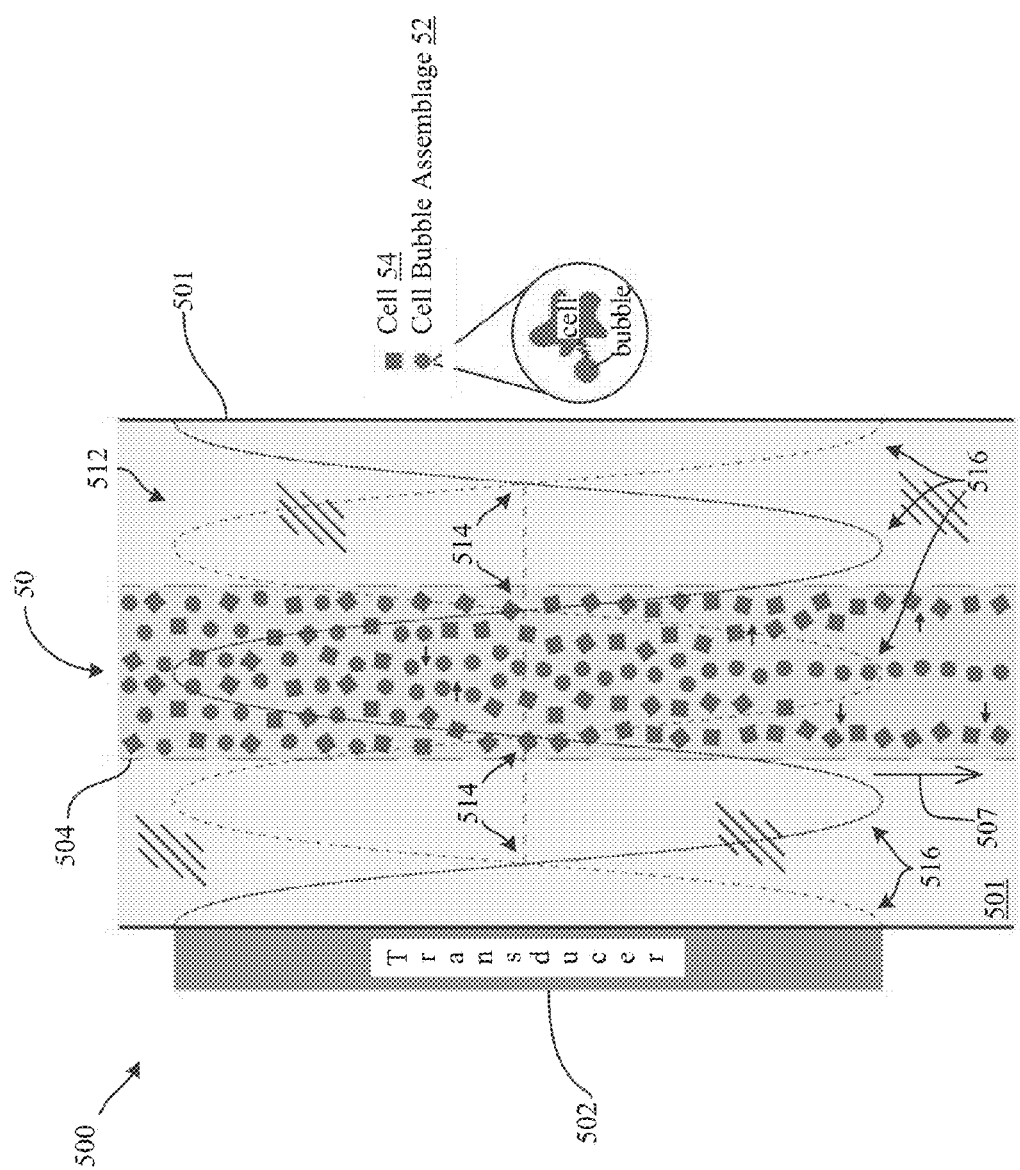
FIG. 5 illustrates another exemplary system for differentiating cells according to many embodiments of the present invention.

FIG. 5 illustrates an exemplary system 500 for differentiating cells. System 500 includes an acoustic transducer 502 acoustically coupled with a flow cell 501. The flow cell 501 includes a flow channel 504 for conducting a sample 50 and directing the sample 50 in direction 507 (or opposite direction). Transducer 502 may be configured to deliver a higher order standing wave 512 transverse to the flow channel 504 compared to the acoustic transducer 302 of system 300. With the higher-order standing wave 512, an antinode 516 may be positioned along the centerline of the flow channel 504 and adjacent nodes 514 may be positioned along the sides of the flow channel 504. In such a configuration, the bubble-cell assemblages 52 will be pushed toward the center of the flow channel 504 while the untagged cells 54 are pushed toward the sides of the flow channel 504 so long as the system is driven below the natural resonance frequency of the bubbles. In some situations, if the system is driven above the natural resonance frequency of the bubbles, then both tagged and untagged cells may be driven in the same direction. In some embodiments, the flow channel 504 may split into three separate sub-channels or reservoirs for storing the bubble-cell assemblages 52 pushed toward the center of the flow channel 504 separate from the untagged cells 54 which were pushed toward the sides of the flow channel 504. In this configuration, the flow channel 504 may be positioned along a centerline of the flow cell 501.

While illustrated as configured with an antinode 516 positioned along a centerline of the flow channel 504, it should be understood that other configurations are possible. For example, in some embodiments systems may be configured with a node 514 positioned along the centerline and adjacent antinodes 516 positioned along the sides of flow channel 504. In such a configuration, the bubble-cell assemblages 52 will be pushed toward the sides of the flow channel 504 while the untagged cells 54 will be pushed slightly toward the centerline of the flow channel 504.

Further, systems described above may be a separate device, or as part of a flow cytometer system in some embodiments. In a flow cytometer, the cell sample 50 may be interrogated with a light source while the cell sample 50 passes through the standing wave or after the cell 52, 54 have been separated by the standing acoustic wave. Sensors may be provided for detecting light scatter from the cells 52, 54 in response to the light interrogation and a coupled processor may be configured to differentiate cells in response to the detected light scatter. Further, sensors may be provided for detecting fluorescence emitted from fluorophore tagged cells in the cell sample in response to the interrogation light and a processor may be configured to further differentiate and/or sort the cells in response to emitted fluorescence.

Figure 6:
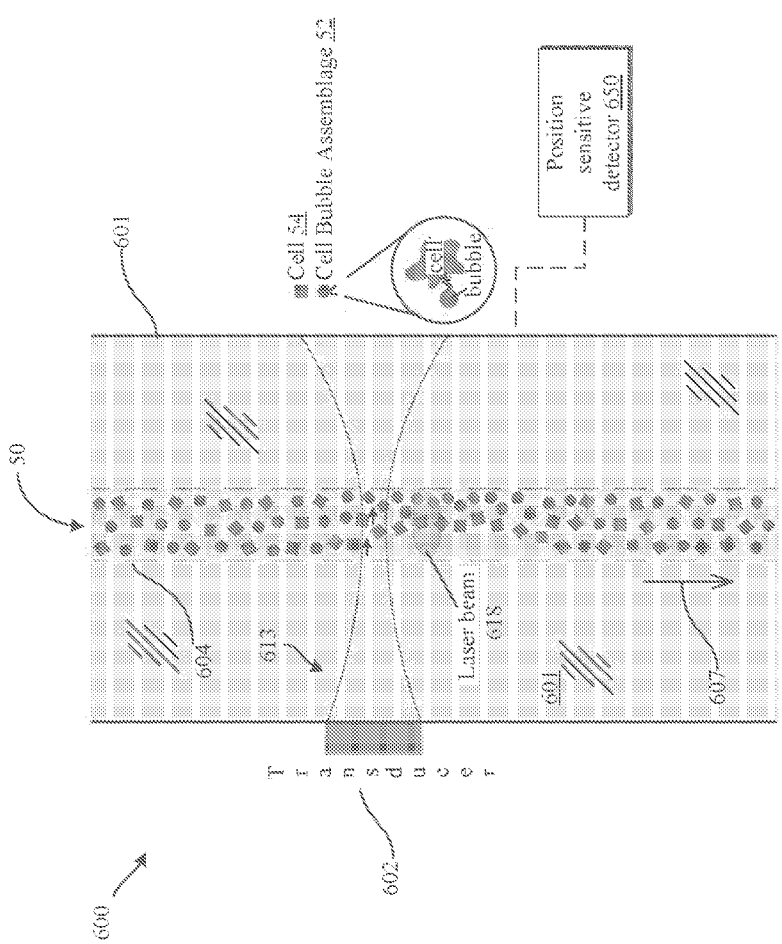
FIG. 6 illustrates another exemplary system for differentiating cells according to many embodiments of the present invention.

FIG. 6 illustrates an exemplary system 600 for differentiating cells using a focused acoustic wave. The system 600 includes an acoustic transducer 602 acoustically coupled with a flow cell 601. The flow cell 601 includes a flow channel 604 for receiving a sample 50 and directing sample 50 in direction 607. Transducer 602 may be configured to deliver a focused acoustic (standing or travelling) wave 613 transverse to the flow channel 604. The focused acoustic wave 613 is used to push all the particles in sample 50. The acoustic radiation force on the bound assemblages 52 will differ greatly from individual cells 54, making it possible to distinguish assemblages 52 from untagged cells 54. Thus, specific cell types may be detected using the systems and methods described above (e.g., position sensitive detector 650). Thereafter, these particles may be further sorted by interrogation by a laser beam 618 as part of a flow cytometer system in many of the methods described above. Alternatively, the specific cells of interest may be sorted and concentrated (enriched) for further characterization or analyzing by downstream instruments or techniques.

In exemplary embodiments, a flow cell may comprise a 7 mm thick polyethylene layer. An attached acoustic transducer may operate at 1.17 MHz. A force plot at 1.17 MHz is shown in FIG. 7. Force is in Newtons, for a 3 µm diameter bubble, generator voltage is 10 V peak-to-peak. The generator output impedance may be 50 Ohm. Positive force means force directed outwards away from the transducer. An exemplary 1 mm width channel 750 is shown. As illustrated a 1 mm width channel may be too wide because it has both positive and negative forces. An exemplary 0.5 mm width channel 760 is shown. The force sign is positive almost everywhere within the channel 760, although the force is close to zero at the edges of channel 760. The maximum force positions for the force plot are 0.154, 0.987, 1.827, 2.66, 3.49, 4.33, 5.16, 6, and 6.82 mm.

Figure 12:
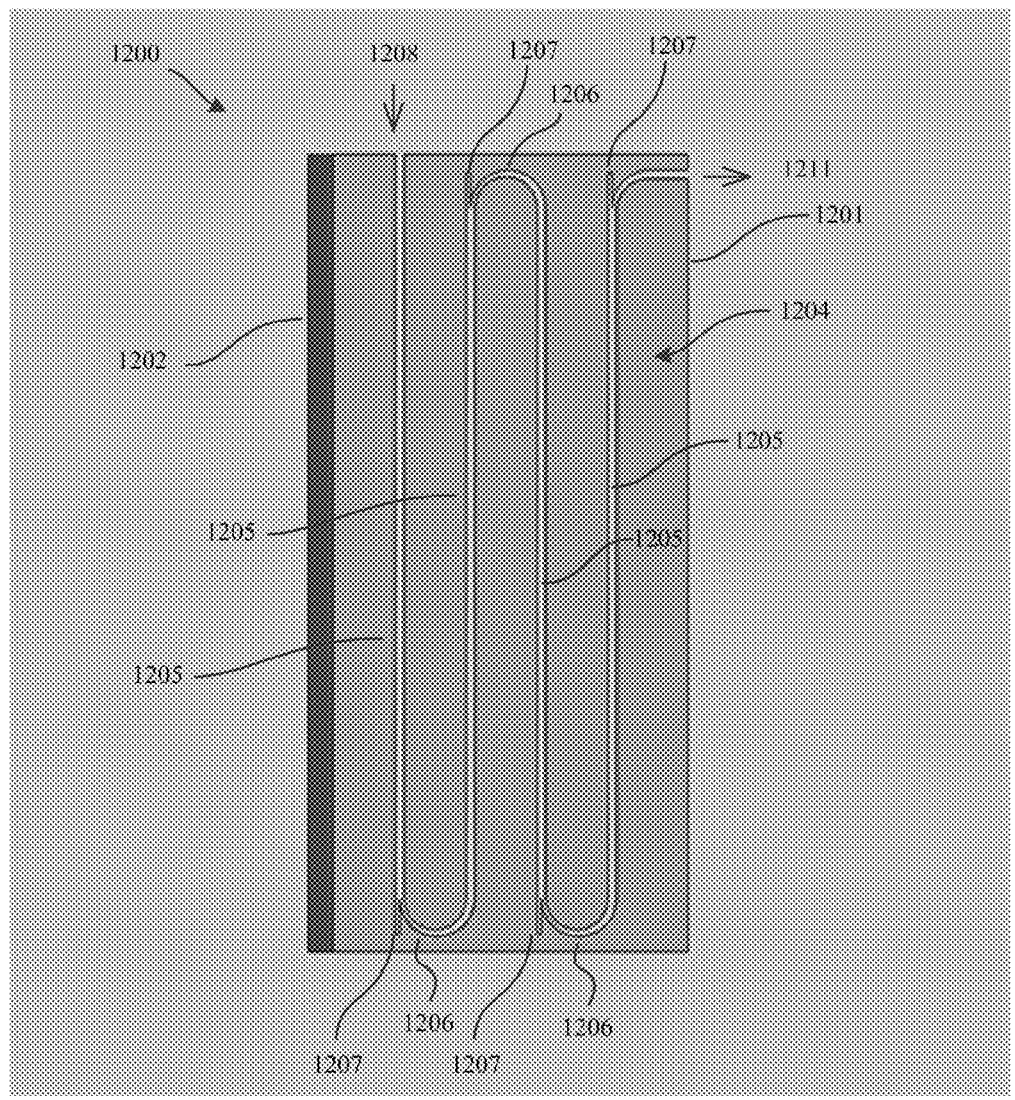
FIG. 12 illustrates another exemplary system for differentiating cells whereby multiple separator segments are employed to more efficiently separate cells of interest
Figure 13:
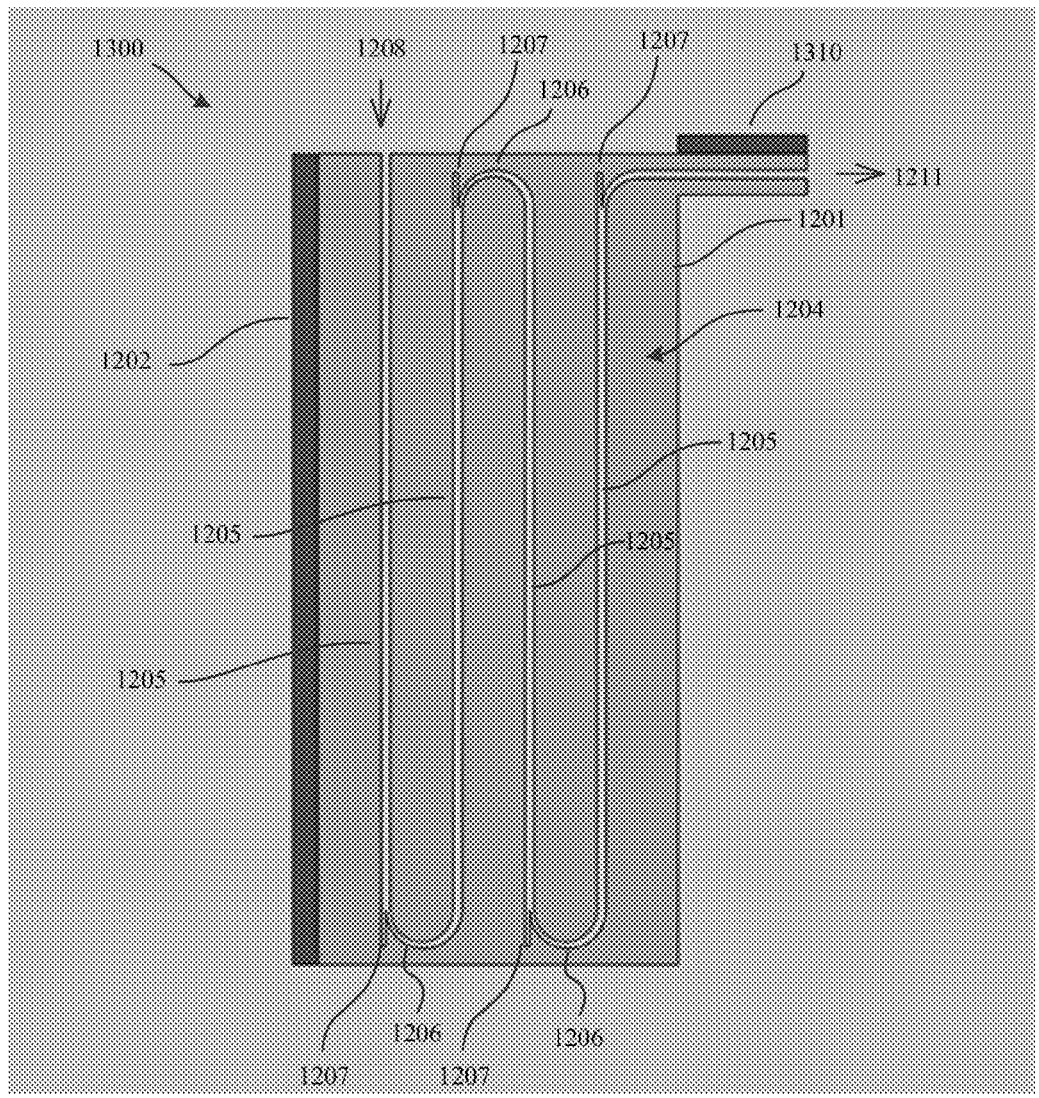
FIG. 13 illustrates another exemplary system where an acoustic transducer may be used to rupture bubbles after the cells or particles of interest are concentrated.
Figure 14:
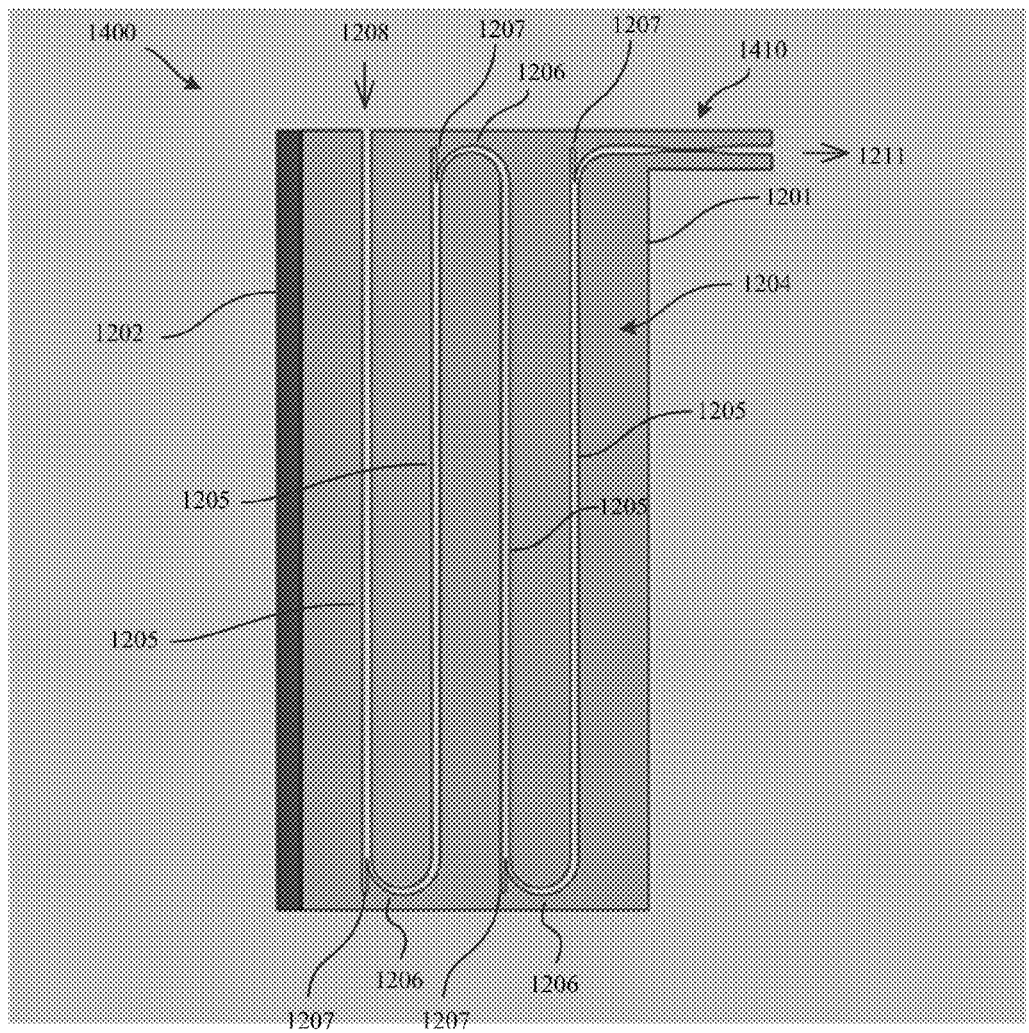
FIG. 14 illustrates another exemplary system where a venture tube outlet configuration may be used to rupture bubbles after the cells or particles of interest are concentrated.

Because the positive forces are at different locations, another exemplary embodiment may use a serpentine flow channel where the channel fingers match the positions of positive force, as described above. FIGS. 12-14 illustrate exemplary serpentine coil systems for repeated separation (enrichment) of cells or particles of interest using a single transducer device. FIG. 12 illustrates an exemplary system 1200. System 1200 includes a flow cell 1201 acoustically coupled with an acoustic source 1202. Flow cell 1201 may include a flow channel 1204 for conducting a sample. The flow channel 1204 may include a number of parallel flow channel segments 1205 connected by flow channel bends 1206. The flow channel segments 1205 may be generally perpendicular to a propagation direction of acoustic source 1202. Prior to or at the start of bends 1206, the flow channels 1204 may split such that a portion of the flow channel segments 1205 may extend past the bends 1206 to form output ports 1207.

A sample may enter in direction 1208. Bubble-cell (or particle) assemblage may be pushed away from the acoustic source 1202 by acoustic waves from the acoustic source 1202. The bubble-cell assemblages follow the serpentine path, while untagged particles are directed and removed via output ports 1207. The fingers of the serpentine coil flow channels 1205 are located where the acoustic forces are positive. The number of output ports 1207 can vary. The final output port 1211 may contain the enriched sample of interest In some embodiments, bubble rupture can take place here. For example, as illustrated in FIG. 13, a system 1300 may include similar features as system 1200 but may also include an acoustic transducer 1310 mounted to the output port 1211. The acoustic transducer 1310 may be configured to subject bubbles to acoustic energy to rupture or destroy bubbles at the output port 1211 thereby further streamlining or automating further analysis or processing of the cells or particles of interest. FIG. 14 illustrates yet another embodiment where bubbles may be ruptured at an output of the flow cell. As illustrated in FIG. 14, a system 1400 may include similar features as system 1200 but output port channel 1211 be configured as a venture tube 1410 such that the diameter change in the channel causes forces on the bubbles to rupture the bubbles. The venture effect may cause the fluid velocity to increase. The corresponding pressure decreases and causes the bubbles to grow and break.

Piezoelectric transducers in 1-D approximation are well studied. In this case the transducer can be considered as a six-pole (FIG. 8). Usually the signs of velocities $v_1$, $v_2$, and forces $F_1$, $F_2$, are considered as positive, when they are directed towards the piezoelectric layer. Also, the electrical current I is positive if it flows into the transducer. The analysis gives the following relationship:

$$\begin{pmatrix} F_1 \\ F_2 \\ U \end{pmatrix} = i \cdot \begin{pmatrix} zA\cotankl & zA/\sin kl & h/\omega \\ zA/\sin kl & zA\cotankl & h/\omega \\ h/\omega & h/\omega & 1/\omega C_0 \end{pmatrix} \cdot \begin{pmatrix} v_1 \\ v_2 \\ I \end{pmatrix}. \quad (1)$$

Here we suppose sinusoidal excitation $\sim e^{-i\omega t}$, cotan=cos/sin. Also, $k=\omega/c$ is the wavenumber in the piezoelectric medium, A is surface area of the transducer active element, and $z=\rho c$: acoustical impedance of the piezoelectric material. $C_o$ is the capacitance of the clamped ($v_1=v_2=0$) transducer:

$$C_0 = \frac{\varepsilon \varepsilon_0 A}{l}, \quad (2)$$

where $\epsilon_0 = 8.85 \cdot 10^{-12}$ F/m, $\epsilon$ is the permittivity of the clamped piezoelectric material, and $$h = \frac{e_{33}}{\varepsilon \varepsilon_0}. \quad (3)$$

Note that [h]=V/m. As a parameter, the electro-mechanical coupling coefficient $k_T$ is frequently used. It is related to $e_{33}$ as follows:

$$k_T = \frac{e_{33}}{\sqrt{\varepsilon \varepsilon_0 \rho c^2}}. \quad (4)$$

Set of equations (1) allows theoretical analysis of the transducer both as a receiver and as a source. We rewrite this set accounting for the fact that F=pS:

$p_1 = iz \cotan kl \cdot v_1 + i(z/\sin kl) \cdot v_2 + i(h/S\omega) \cdot I$ $p_2 = i(z/\sin kl) \cdot v_1 + iz \cotan kl \cdot v_2 + i(h/S\omega) \cdot I$ $U = i(h/\omega) \cdot v_1 + i(h/\omega) \cdot v_2 + (i/\omega C_0) \cdot I \quad (1a)$ Let us suppose that we know the impedances on both sides of the piezoelectric plate: $p_1/v_1 = -z_1$ и $p_2/v_2 = -z_2$. For instance, if the side #1 is contacting a semi-infinite medium, then $z_1$ is this medium's acoustical impedance (i.e., $z_1 = \rho_1 c_1$). If the side #1 is in contact with a layered structure, then $z_1$ is no longer given by $\rho_1 c_1$, but is instead an impedance of the corresponding layer. Actually, the nature of the impedance $z_1$ is not important: the resultant formulas depend only on value $z_1$. Keeping that in mind the fact that $p_1/v_1 = -z_1$, $p_2/v_2 = -z_2$ may be used. Then the set (1a) becomes:

$$p_1 = -i\frac{z}{z_1}\cotan kl \cdot p_1 - i\frac{z}{z_2}(1/\sin kl) \cdot p_2 + i(h/S\omega) \cdot I \quad (1b)$$

$$p_2 = -i\frac{z}{z_1}(1/\sin kl) \cdot p_1 - i\frac{z}{z_2}\cotan kl \cdot p_2 + i(h/S\omega) \cdot I$$

$$U = -i(h/\omega) \cdot \frac{p_1}{z_1} - i(h/\omega) \cdot \frac{p_2}{z_2} + i(1/\omega C_0) \cdot I.$$

From the first and second equations of this set, pressure amplitudes $p_1$, $p_2$ may be derived as functions of the current, I:

$$p_1 = \frac{(ih/S\omega) \cdot \left[1 + i\frac{z}{z_2}\cotan kl - i\frac{z}{z_2}(1/\sin kl)\right]}{\left(1 + i\frac{z}{z_1}\cotan kl\right) \cdot \left(1 + i\frac{z}{z_2}\cotan kl - i\frac{z}{z_2}(1/\sin kl)\right) + i\frac{z}{z_2}(1/\sin kl)\left(1 + i\frac{z}{z_1}\cotan kl - i\frac{z}{z_1}(1/\sin kl)\right)} \cdot I$$

$$p_2 = \frac{(ih/S\omega) \cdot \left[1 + i\frac{z}{z_1}\cotan kl - i\frac{z}{z_1}(1/\sin kl)\right]}{\left(1 + i\frac{z}{z_1}\cotan kl\right) \cdot \left(1 + i\frac{z}{z_2}\cotan kl - i\frac{z}{z_2}(1/\sin kl)\right) + i\frac{z}{z_2}(1/\sin kl)\left(1 + i\frac{z}{z_1}\cotan kl - i\frac{z}{z_1}(1/\sin kl)\right)} \cdot I.$$

The denominator, after opening the brackets, can be written in a shorter form:

$$1 + \frac{z^2}{z_1 z_2} + iz\frac{z_1 + z_2}{z_1 z_2}\cotan kl.$$

Therefore, $$p_1 = \frac{ih}{S\omega} \cdot \frac{1 + i\frac{z}{z_2}\cotan kl - i\frac{z}{z_2}(1/\sin kl)}{1 + \frac{z^2}{z_1 z_2} + iz\frac{z_1 + z_2}{z_1 z_2}\cotan kl} \cdot I \quad (1c)$$

-continued $$p_2 = \frac{ih}{S\omega} \cdot \frac{1 + i\frac{z}{z_1}\cotan kl - i\frac{z}{z_1}(1/\sin kl)}{1 + \frac{z^2}{z_1 z_2} + iz\frac{z_1 + z_2}{z_1 z_2}\cotan kl} \cdot I.$$

Putting these expressions into the third equation of the set (1b), the following equation can be obtained:

$$U = \left\{ \frac{\frac{(h/\omega)^2}{S}\left[\frac{1}{z_1}\cdot\left(1 + i\frac{z}{z_2}\cotan kl - i\frac{z}{z_2}(1/\sin kl)\right) + \frac{1}{z_2}\cdot\left(1 + i\frac{z}{z_1}\cotan kl - i\frac{z}{z_1}(1/\sin kl)\right)\right]}{1 + \frac{z^2}{z_1 z_2} + iz\frac{z_1 + z_2}{z_1 z_2}\cotan kl} + \frac{i}{\omega C_0} \right\} \cdot I.$$

After making multiplications in the numerator, a shorter expression may be obtained:

$$U = \left\{ \frac{-i\frac{(h/\omega)^2}{S}\frac{z}{z_1 z_2}\left[i\frac{z_1+z_2}{z} + 2\frac{1-\cos kl}{\sin kl}\right]}{1 + \frac{z^2}{z_1 z_2} + iz\left(\frac{z_1+z_2}{z_1 z_2}\right)\cotan kl} + \frac{i}{\omega C_0} \right\} \cdot I.$$

From here, the transducer electrical impedance, $Z_0$ may be obtained:

$$Z_0 \equiv \frac{U}{I} = \frac{i}{\omega C_0} \cdot \left\{ 1 - \frac{\omega C_0 \frac{(h/\omega)^2}{zS}\left[i\frac{z_1+z_2}{z}\cdot\sin kl + 2(1-\cos kl)\right]}{\left(1 + \frac{z_1 z_2}{z^2}\right)\cdot\sin kl + i\frac{z_1+z_2}{z}\cos kl} \right\}.$$

Note that $C_0 = \epsilon_0 \epsilon S/l$. Then $$\omega C_0 \frac{(h/\omega)^2}{S} = \frac{\epsilon_0 \epsilon h^2}{\omega l} = \frac{\epsilon_0 \epsilon h^2}{c(\omega/c)l} = \frac{1}{kl}\frac{\epsilon_0 \epsilon h^2}{c}.$$

We will also use the previously mentioned expressions:

$$k_T = e_{z3}/\sqrt{\epsilon_0 \epsilon \rho c^2} \text{ и } h = \frac{e_{z3}}{\epsilon_0 \epsilon}.$$

From them, $$\frac{\epsilon_0 \epsilon h^2}{c} = \frac{1}{c}\frac{e_{z3}^2}{\epsilon_0 \epsilon} = \frac{1}{c}\frac{k_T^2 \epsilon_0 \epsilon \rho c^2}{\epsilon_0 \epsilon} = z \cdot k_T^2.$$

Finally, we come to the following expression:

$$Z_0 = \frac{1}{-i\omega C_0} \cdot \left[1 - \frac{k_T^2}{kl} \cdot \frac{i\frac{z_1+z_2}{z}\sin kl + 2(1-\cos kl)}{\left(1 + \frac{z_1 z_2}{z^2}\right)\sin kl + i\frac{z_1+z_2}{z}\cos kl}\right]. \quad (5)$$

Let us consider an electrical source with an output impedance r, usually r=50 Ohm. If $U_0$ is its voltage setting, then the voltage at the piezoelectric transducer is $$U = U_0 \frac{Z_0}{Z_0 + r}. \quad (6)$$

We can relate this voltage with the radiating pressure amplitude using Eq. (1c) and the fact that $I = U/Z_0$. For instance, for $p_1$ we get:

$$\frac{p_1}{U_0} = \frac{ih}{S\omega} \cdot \frac{1 + i\frac{z}{z_2}\cotan kl - i\frac{z}{z_2}(1/\sin kl)}{1 + \frac{z^2}{z_1 z_2} + iz\frac{z_1+z_2}{z_1 z_2}\cotan kl} \cdot \frac{1}{Z_0 + r}. \quad (7)$$

Consider a particular case when one of the sides (say, side 2) of the piezoelectric plate is pressure-released. Then $z_2=0$, and we have:

$$Z_0 = \frac{1}{-i\omega C_0} \cdot \left[1 - \frac{k_T^2}{kl} \cdot \frac{i\frac{z_1}{z}\sin kl + 2(1-\cos kl)}{\sin kl + i\frac{z_1}{z}\cos kl}\right], \quad (5a)$$

and $$\frac{p_1}{U_0} = \frac{h}{S\omega} \cdot \frac{1 - \cos kl}{\frac{z}{z_1}\sin kl + i\cos kl} \cdot \frac{1}{Z_0 + r}. \quad (7a)$$

Note that in Eq. (7a), $$\frac{h}{S} = \frac{k_T \sqrt{\epsilon \epsilon_0 \rho c^2}}{C_0 l},$$

so it can be written as:

$$\frac{p_1}{U_0} = \frac{k_T \sqrt{\epsilon \epsilon_0 \rho}}{C_0} \cdot \frac{1}{kl} \cdot \frac{1 - \cos kl}{\frac{z}{z_1}\sin kl + i\cos kl} \cdot \frac{1}{Z_0 + r}. \quad (7b)$$

Standing Waves in a Layer

Now consider a situation when the transducer is loaded by a layer of thickness L as illustrated in FIG. 9, with density, sound speed, and absorption coefficient $c_1$, $\rho_1$, and $\alpha_1$. Note that the wavenumber in such a medium is complex:

$$k_1 = \frac{\omega}{c_1} + i\alpha_1.$$

Suppose that the distal side of the layer is pressure-released. The boundary conditions are $p(x=0)=p_1$ and $p(x=L)=0$. The wave equation solutions for acoustic pressure $p(x)$ and particle velocity $v(x)$ complex amplitudes are:

$$p(x) = p_1 \frac{e^{ik_1 x} - e^{ik_1(2L-x)}}{1 - e^{2ik_1 L}}, \quad (8)$$

and

-continued $$v(x) = \frac{p_1}{\rho_1 c_1} \frac{e^{ik_1 x} + e^{ik_1(2L-x)}}{1 - e^{2ik_1 L}}. \quad (9)$$

From here we find acoustic impedance of the layer at the distal interface:

$$z_1 = \frac{p(0)}{v(0)} = \rho_1 c_1 \cdot \frac{1 - e^{2ik_1 L}}{1 + e^{2ik_1 L}}. \quad (10)$$

This parameter is present in Eqs. (5a) and (7b). Therefore, the pressure distribution in the layer depends on frequency in a fairly complicated way: we need to use Eq. (8) with $$k_1 = \frac{\omega}{c_1} + i\alpha_1(\omega),$$

then use Eq. (7b) for $p_1$, where we should use Eq. (5a) for $Z_0$, and in all those equations we should use $z_1$ from Eq. (10).

Forced Bubble Oscillation

Let us consider a bubble that linearly oscillates in the acoustic pressure field $$P(x, t) = \frac{p(x)}{2} e^{-i\omega t} + \frac{p^*(x)}{2} e^{i\omega t}. \quad (11)$$

The bubble radius is $R(x,t)=R_0+\tilde{R}(x,t)$, where $R_0$ is equilibrium radius, and $\tilde{R}$ is its variation. The linearized equation for the bubble radius is:

$$\ddot{\tilde{R}} + 2\delta\dot{\tilde{R}} + \omega_0^2 \tilde{R} = -\frac{P(x, t)}{\rho_1 R_0}. \quad (12)$$

Here the decrement $\delta$ characterizes energy attenuation during the bubble oscillation. The stationary solution of Eq. (12) is:

$$\tilde{R} = \frac{A}{2} e^{-i\omega t} + \frac{A^*}{2} e^{i\omega t}, \quad (13)$$

where the complex amplitude is $$A = \frac{p}{\rho_1 R_0} \cdot \frac{1}{\omega^2 - \omega_0^2 + i2\delta\omega}.$$

It is convenient to introduce the bubble quality factor $Q=\omega_0/\delta$ (typically $Q\approx 10$), and write:

$$A = \frac{p}{\rho_1 R_0} \cdot \frac{1}{\omega^2 - \omega_0^2 + 2i\frac{\omega\omega_0}{Q}}. \quad (14)$$

Radiation Force on a Bubble

Radiation force on a bubble can be expressed as follows: $F=-\langle V\nabla P\rangle$, where $\langle\cdot\rangle$ indicates averaging over a cycle, $V=4/3\pi R^3$ is bubble volume. In the 1-D case, $$F = -\left\langle V\frac{\partial P}{\partial x}\right\rangle.$$

In the linear approximation, $V\approx 4/3\pi R_0^3 + 4\pi_0^2 \tilde{R}$. As a result we can write:

$$F = -4\pi R_0^2 \left\langle \tilde{R}\frac{\partial P}{\partial x}\right\rangle. \quad (15)$$

Therefore, $$F = -\frac{2\pi R_0}{\rho_1} \text{Re}\left(p^* \cdot \frac{dp}{dx} \cdot \frac{1}{\omega^2 - \omega_0^2 + 2i\frac{\omega\omega_0}{Q}}\right). \quad (16)$$

Using Eq. (14), we express the radiation force through acoustic pressure complex amplitude:

$$F = -2\pi R_0^2 \text{Re}\left(\frac{dp}{dx} A^*\right).$$

Consider the case when the frequency is much lower or much higher than the bubble resonance frequency. Then $$\omega^2 - \omega_0^2 + 2i\frac{\omega\omega_0}{Q} \approx \omega^2 - \omega_0^2,$$

and $$F\bigg|_{\substack{\omega\ll\omega_0\\\omega\gg\omega_0}} = -\frac{\pi R_0}{\rho_1} \frac{1}{\omega^2 - \omega_0^2} \frac{d(|p|^2)}{dx}. \quad (16a)$$

From here it is seen that for small bubbles ($\omega<\omega_0$), the force $F\sim d(|p|^2)/dx$; i.e., such bubbles are moved towards pressure node. For large bubbles ($\omega>\omega_0$), the force $F\sim -d(|p|^2)/dx$, i.e.; such bubbles are moved towards the pressure antinode.

Some Simplified Expressions

From Eq. (8), $$|p|^2 = |p_1|^2 \frac{e^{-2\alpha_1 x} + e^{-2\alpha_1(2L-x)} - 2e^{-\alpha_1(2L-x)}\cos\left(2\frac{\omega}{c_1}(L-x)\right)}{1 + e^{-4\alpha_1 L} - 2e^{-2\alpha_1 L}\cos\left(2\frac{\omega}{c_1}L\right)} \quad (17)$$

From here, $$\frac{d(|p|^2)}{dx} = |p_1|^2 \frac{2\alpha_1 \left[ \begin{array}{c} -e^{-2\alpha_1 x} + e^{-2\alpha_1(2L-x)} - \\ e^{-\alpha_1(2L-x)}\cos\left(2\frac{\omega}{c_1}(L-x)\right) \end{array} \right] - 4\frac{\omega}{c_1}e^{-\alpha_1(2L-x)}\sin\left(2\frac{\omega}{c_1}(L-x)\right)}{1 + e^{-4\alpha_1 L} - 2e^{-2\alpha_1 L}\cos\left(2\frac{\omega}{c_1}L\right)}.$$

Consider low-attenuation case, when $$\alpha \ll \frac{\omega}{c_1}.$$

Then $$\frac{d(|p|^2)}{dx} \approx |p_1|^2 \frac{2\frac{\omega}{c_1}\sin\left(2\frac{\omega}{c_1}(x-L)\right)}{1 + e^{-4\alpha_1 L} - 2e^{-2\alpha_1 L}\cos\left(2\frac{\omega}{c_1}L\right)}.$$

From here and Eq. (16a), we find the maximum force:

$$(\max F)\bigg|_{\substack{\omega \ll \omega_0 \\ \omega \gg \omega_0}} = \frac{2\pi R_0}{\rho_1 c_1} \frac{|p_1|^2 \omega}{|\omega^2 - \omega_0^2|} \frac{1}{1 + e^{-4\alpha_1 L} - 2e^{-2\alpha_1 L}\cos\left(2\frac{\omega}{c_1}L\right)}. \quad (18)$$

We remind the reader that here $p_1(\omega)$, and its dependence on frequency is also of resonance nature. If we use the corresponding equation for $p_1(\omega)$, we can find the optimal frequency that creates the largest radiation force.

Figure 11:
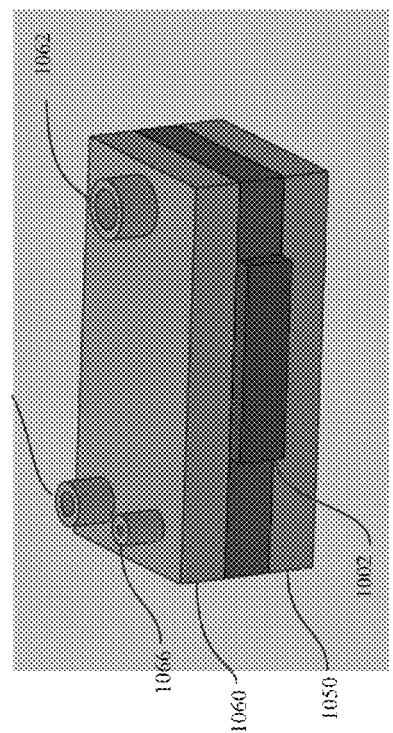
FIG. 11 illustrates the exemplary system of FIG. 10 once the components are assembled.
Figure 10:
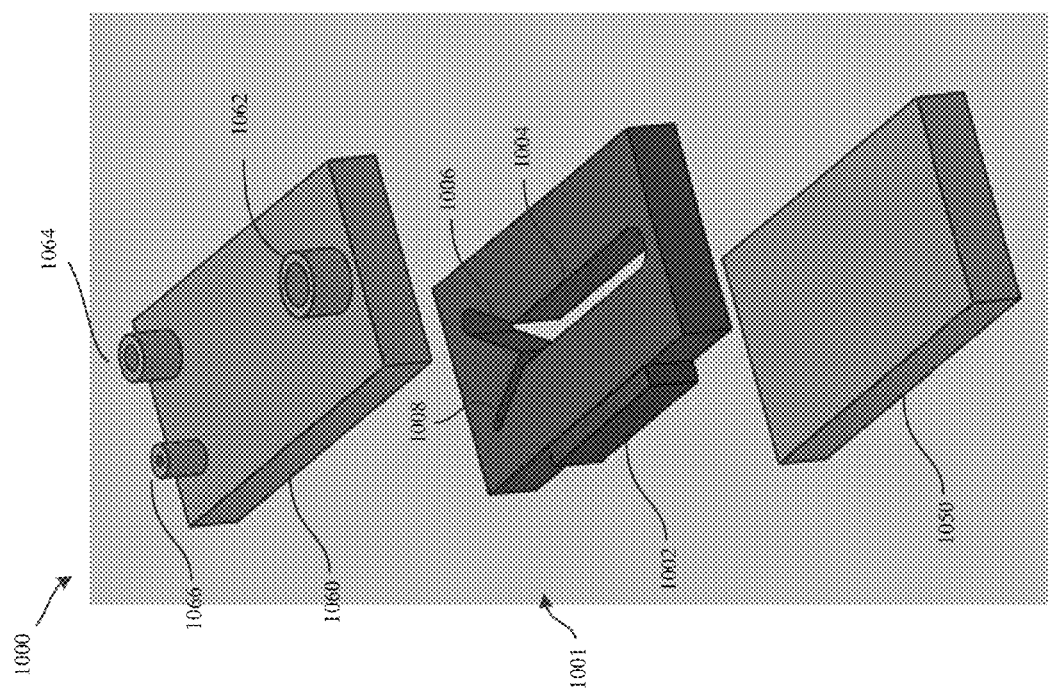
FIG. 10 illustrates an exploded view of an exemplary system for differentiating cells.

FIG. 10 illustrates an exploded view of an exemplary system 1000 for differentiating cells. System 1000 includes a flow cell 1001 acoustically coupled with an acoustic transducer 1002. The flow cell 1001 includes a flow channel 1004 for receiving and separating a sample. Flow channel 1004 splits into two sub-channels or reservoirs, 1006, 1008 for separately storing portions of a cell sample from a remaining portion of the cell sample. In some embodiments, flow cell 1001 includes an bottom component 1050 defining a bottom surface of the flow channel 1004 and an upper component 1060 defining an upper surface of the flow channel 1004. The upper component 1060 may include an input port 1062 for inserting a sample into the flow cell 1001 at an upstream location of the flow channel 1004. The upper component 1060 may further include an extraction port 1064 for removing a separated portion (for example, tagged cells) of interest at a downstream portion of the flow channel 1004 at reservoir 1006. A separate extraction port 1066 may be provided in upper component 1060 for removing a second portion (for example, untagged cells) of the separated sample from the downstream portion of the flow channel 1004 at reservoir 1008. FIG. 11 illustrates the exemplary system 1000 of FIG. 10 once the components are assembled.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A system for separating particles of interest from a sample, the system comprising:
   one or more acoustic transducers sources;
   a flow cell acoustically coupled with the acoustic transducer source, the flow cell having a flow channel therethrough for receiving and conducting a sample;
   wherein the acoustic transducer sources is positioned and configured to deliver a standing wave transverse to the flow channel, the standing wave having at least one pressure node and adjacent pressure antinode; and
   wherein a centerline of the flow channel is offset from positioned between the at least one pressure node and pressure antinode of the standing wave such that a pressure gradient extends transverse to the centerline of the flow channel when the acoustic transducer delivers the standing wave;

wherein the standing wave delivered by the acoustic transducer includes only one pressure node or pressure antinode, and wherein the flow channel is offset from a centerline of the flow cell.

2. The system of claim 1, wherein a downstream portion of the flow channel splits into two sub-channels for separating cells of interest from a remainder of the conducted sample.

3. The system of claim 1, further comprising a light source configured to emit an interrogation light to the conducted sample after applying the standing wave to the conducted sample.

4. The system of claim 3, further comprising a sensor for capturing light scattered by the conducted sample in response to the interrogation light thereby producing a signal indicative of a vibrational effect experienced by particles of the conducted sample in response to the acoustic wave; and further comprising a processor coupled to the sensor, the processor configured to analyze the signal to identify particles within the sample based on the vibration effect experienced by the particles in response to the acoustic wave.

5. The system of claim 3, further comprising a sensor for capturing fluorescing light from particles of the conducted sample in response to the interrogation light thereby producing a signal indicative of an attached fluorophore; and further comprising a processor coupled to the sensor, the processor configured to separate particles based on the detection of attached fluorophores.

6. The system of claim 1, wherein a second acoustic transducer is acoustically coupled with the flow cell at a downstream portion of the flow channel, wherein the second acoustic transducer is configured to deliver acoustic energy toward the downstream portion of the flow channel to rupture bubbles at the downstream portion.

7. The system of claim 1, wherein the flow channel comprises an outlet port channel configured as a venturi tube, the venturi tube configured to rupture bubbles at the outlet port channel.

8. A system for separating particles of interest from a sample, the system comprising:
   one or more acoustic transducers sources;
   a flow cell acoustically coupled with the acoustic transducer source, the flow cell having a flow channel therethrough for receiving and conducting a sample;
   wherein the acoustic transducer sources is positioned and configured to deliver a standing wave transverse to the flow channel, the standing wave having at least one pressure node and adjacent pressure antinode; and
   wherein a centerline of the flow channel is offset from positioned between the at least one pressure node and pressure antinode of the standing wave such that a pressure gradient extends transverse to the centerline of the flow channel when the acoustic transducer delivers the standing wave;
   a position sensitive detector configured to detect the translation of particles of interest in response to the standing wave.

9. A system for separating cells of interest from a sample, the system comprising:
   an acoustic transducer source;
   a flow cell acoustically coupled with the acoustic transducer source, the flow cell having a flow channel therethrough for receiving a sample;
   wherein the acoustic transducer source is positioned and configured to deliver an acoustic wave transverse to the flow channel; and
   a position sensitive detector configured to selectively detect the cells of interest in response to translation of the cells of interest in a direction transverse to an axis of the flow channel by the acoustic wave.

10. The system of claim 9, wherein the sample comprises a cell sample with the cells of interest and other cells, wherein the flow cell and acoustic detector are configured to separate the cells of interest from the other cells using bubbles selectively tagged to the cells of interest.

11. The system of claim 9, wherein a second acoustic transducer is acoustically coupled with the flow cell at a downstream portion of the flow channel, wherein the second acoustic transducer is configured to deliver acoustic energy toward the downstream portion of the flow channel to rupture bubbles at the downstream portion.

12. The system of claim 9, wherein the flow channel comprises an outlet port channel configured as a venturi tube, the venturi tube configured to rupture bubbles at the outlet port channel.

* * * * *